United States Patent
Li et al.

(10) Patent No.: US 10,029,121 B2
(45) Date of Patent: Jul. 24, 2018

(54) SYSTEM AND METHOD FOR PRODUCING SYNTHETIC IMAGES

(71) Applicant: THE MEDICAL COLLEGE OF WISCONSIN, INC., Milwaukee, WI (US)

(72) Inventors: X. Allen Li, Milwaukee, WI (US); Eric S. Paulson, Milwaukee, WI (US); Ergun Ahunbay, Milwaukee, WI (US); Cun-geng Yang, Milwaukee, WI (US); Vern Hart, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 79 days.

(21) Appl. No.: 15/108,188

(22) PCT Filed: Dec. 30, 2014

(86) PCT No.: PCT/US2014/072645
§ 371 (c)(1),
(2) Date: Jun. 24, 2016

(87) PCT Pub. No.: WO2015/103184
PCT Pub. Date: Jul. 9, 2015

(65) Prior Publication Data
US 2016/0310761 A1 Oct. 27, 2016

Related U.S. Application Data

(60) Provisional application No. 61/922,343, filed on Dec. 31, 2013.

(51) Int. Cl.
*G06K 9/00* (2006.01)
*A61N 5/10* (2006.01)
(Continued)

(52) U.S. Cl.
CPC ............ *A61N 5/1039* (2013.01); *A61B 5/055* (2013.01); *A61B 5/4836* (2013.01);
(Continued)

(58) Field of Classification Search
None
See application file for complete search history.

(56) References Cited

U.S. PATENT DOCUMENTS

2002/0150207 A1 10/2002 Kapatoes et al.
2006/0259282 A1 11/2006 Failla et al.
(Continued)

OTHER PUBLICATIONS

International Search Report dated May 20, 2015 for International Application No. PCT/US2014/072645.

*Primary Examiner* — Idowu O Osifade
(74) *Attorney, Agent, or Firm* — Quarles & Brady LLP

(57) ABSTRACT

Systems and methods directed to adaptive radiotherapy planning are provided. In some aspects, provided system and method include producing synthetic images from magnetic resonance data using relaxometry maps. The method includes applying corrections to the data and generating relaxometry maps therefrom. In other aspects, a method for adapting a radiotherapy plan is provided. The method includes determining an objective function based on dose gradients from an initial dose distribution, and generating an optimized plan based on updated images, using aperture morphing and gradient maintenance algorithms without need for organ-at-risk contouring. In yet other aspects, a method for obtaining 4D MR imaging using a temporal reshuffling of data acquired during normal breathing, a method for deformable image registration using a sequentially applied semi-physical model regularization method for multimodality images, and a method to generate 4D plans using an aperture morphing algorithm based on 4D CT or 4D MR imaging are provided.

20 Claims, 23 Drawing Sheets

(51) Int. Cl.
*A61B 5/055* (2006.01)
*A61B 5/00* (2006.01)
*G06K 9/52* (2006.01)
*G06K 9/62* (2006.01)
*G06T 11/00* (2006.01)
*G06T 7/11* (2017.01)
*A61B 6/03* (2006.01)
*A61B 6/00* (2006.01)
*A61B 8/00* (2006.01)
*A61B 8/08* (2006.01)

(52) U.S. Cl.
CPC ......... *A61N 5/1037* (2013.01); *A61N 5/1038* (2013.01); *G06K 9/52* (2013.01); *G06K 9/6267* (2013.01); *G06T 7/11* (2017.01); *G06T 11/003* (2013.01); *A61B 5/7289* (2013.01); *A61B 6/032* (2013.01); *A61B 6/037* (2013.01); *A61B 6/4417* (2013.01); *A61B 6/5247* (2013.01); *A61B 8/4416* (2013.01); *A61B 8/483* (2013.01); *A61B 8/5261* (2013.01); *G06T 2207/10012* (2013.01); *G06T 2207/10076* (2013.01); *G06T 2207/10081* (2013.01); *G06T 2207/10088* (2013.01)

(56) References Cited

U.S. PATENT DOCUMENTS

| | | |
|---|---|---|
| 2009/0022383 A1 | 1/2009 | Falco et al. |
| 2009/0110145 A1 | 4/2009 | Lu et al. |
| 2011/0075806 A1 | 3/2011 | Nord et al. |
| 2012/0223710 A1 | 9/2012 | Palma et al. |
| 2012/0245453 A1* | 9/2012 | Tryggestad ............ A61B 6/463 600/413 |
| 2012/0323112 A1* | 12/2012 | Jokerst ................ A61K 49/225 600/420 |
| 2013/0111101 A1 | 5/2013 | Yoon |
| 2013/0245425 A1 | 9/2013 | Dempsey |

* cited by examiner

Superficial basal cell carcinoma (BCC) lesion on left thigh a). CT b). HFUS c). Enlarged view of a)

d). Enlarged view of b)

e). Histogram-mapped image f). Contrast-enhanced image g). Registered image #1 h). Registered image #2

SYSTEM AND METHOD FOR PRODUCING SYNTHETIC IMAGES

CROSS-REFERENCE TO RELATED APPLICATIONS

This application is a 371 Application of PCT/US2014/072645 filed Dec. 30, 2014 which claims the benefit of U.S. Provisional Patent Application Ser. No. 61/922,343, filed on Dec. 31, 2013, both of which are incorporated herein by reference for all purposes.

BACKGROUND

The present disclosure relates generally to tools, systems and methods for use in radiotherapy treatment delivery and, in particular, to systems and methods for multi-modality imaging-based adaptive planning.

Radiation therapy (RT) has gone through a series of technological revolutions in the last few decades. With intensity modulated RT (IMRT), it became possible to produce highly conformal dose distributions, whereby the bulk radiation dose is delivered within the extent of a tumor. These techniques utilize 3D anatomic and biological information extracted from images of various types (e.g., CT, MRI, PET) acquired a few days prior to the first treatment. However, the locations, shapes and sizes as well as biological properties of the tumor(s), and normal anatomy have been found to change during the course of treatment, primarily due to daily positioning uncertainties of various ROIs and anatomic, physiological and/or clinical factors. The latter include tumor shrinkage, weight loss, volumetric changes in normal organs, non-rigid variations in different bony structures. The traditional assumption that the anatomy discerned from 3D CT images acquired for planning purposes prior to the treatment course is applicable for every fraction may not adequately account for the inter-fractional changes and may limit the ability to fully exploit the potential of highly conformal treatment modalities such as IMRT. This improved capability in dose conformality necessitates better localization of target and organs at risks (OAR), as well as the ability to adapt to inter- or intra-fractional changes, both in the design and in delivery of treatments.

Accurate delivery of radiation therapy necessitates, as a prerequisite, high fidelity, 3D, anatomical images of the patient. For close to two decades, RT planning has utilized CT images as a basis for radiation dose calculation. Due to the linear relationship between Hounsfield units and underlying tissue electron density, CT images permit a voxel-wise correction of radiation dose for differences in tissue attenuation, as well as generation of beam's eye view digitally reconstructed radiographs (DRRs) for treatment verification. The formation of image contrast in CT is primarily due to photoelectric interactions. This effect results in high contrast between tissues of considerably different densities (e.g., bone, lung, and soft tissue). However, adjacent soft tissues (e.g., in brain or abdominal regions) do not possess substantial density differences. The ensuing poor soft tissue contrast on CT images makes delineation of both targets and critical structures extremely challenging. This inability to reliably delineate tumor targets and proximal critical structures on CT images has significant clinical consequences, in that it demands the use of larger margins, which precludes the ability to safely escalate radiation doses due to toxicity constraints of critical structures.

Magnetic resonance imaging (MRI) provides powerful imaging capabilities for cancer diagnosis and treatment. Contrary to CT, MRI is non-ionizing, offers superior soft tissue contrast, and provides a wide array of functional contrast forming mechanisms to characterize tumor physiology. However, unlike CT, the MRI signal bears no direct relationship to electron density, which prevents MRI from being used as a basis for dose calculation. In addition, MR images can be confounded by spatial distortions arising from gradient nonlinearities as well as off-resonance effects. These distortions can be severe, ranging up to several centimeters. Moreover, MR images commonly exhibit regions of non-uniform image intensities, which can introduce inaccuracies in image registration and image segmentation algorithms frequently employed during radiation treatment planning and delivery. These non-uniform image intensities arise out of inhomogeneities in the B1+ (RF transmit) field and B1− (RF receive) field when phased-array coils are used for signal reception. Consequently, despite the obvious soft tissue contrast advantages MRI provides, these current issues (e.g., lack of electron density information, sources of geometric distortion, and signal non-uniformities) have hindered the establishment of MRI as a primary imaging modality in radiation oncology.

Adaptive Radiation Therapy (ART) is a state-of-the-art approach that uses a feedback process to account for patient-specific anatomic and/or biological changes during the treatment, thus, delivering highly individualized radiation therapy for cancer patients. Basic components of ART include: (1) detection of anatomic and biological changes, often facilitated by multi-modality images (e.g., CT, MRI, PET), (2) treatment plan optimization to account for the patient-specific spatial morphological and biological changes with consideration of radiation responses, and (3) technologies to precisely deliver the optimized plan to the patient. Interventions of ART may consist of both online and offline approaches.

The inter- and intra-fractional variations, if not accounted for, could result in sub-optimal dose distributions and significant deviations from the original plan, with potentially negative impact in treatment efficiency. Recently, image guided RT (IGRT) has been used widely to correct (eliminate or reduce) the deteriorating effects of the inter-fractional variations. A wide range of correction strategies has been developed based on the available IGRT technologies. The correction methods can be generally classified as "online" or "offline" approaches. Corrections to patient treatment parameters that are performed right after the daily patient information is acquired and before the daily treatment dose is delivered are classified as "online" corrections. This is in contrast to an "offline" correction where the corrective action is made after the daily treatment has been delivered affecting the treatments of subsequent days. Therefore, when an online correction is applied, the delivered daily dose will be the corrected one using the very latest patient set up and anatomic information.

When a patient is set up for each fraction, the anatomy may be different from the one used for the initial treatment planning. Typically the deviations that are most harmful are the so called "systematic" ones, which are also relatively easier to account for by either an offline or online correction strategy. The random component of the deviations, although sometimes less harmful than the systematic deviations, are generally difficult to be fully accounted for and requires an online correction strategy. One of the advantages of online correction strategies over the offline methods is that online strategies can correct for both systematic and random variations. In addition, offline corrections may not be applicable to a course of therapy with a small number of treatment fractions, such as hypo-fractionation or stereotactic body RT (SBRT).

The chief challenge for an online correction strategy is that it needs to be performed within an acceptable timeframe while the patient is lying on the treatment table in the treatment position. This requirement limits a variety of corrective actions that are used as online strategies in today's technology. Consequently, online correction of inter-fractional variations by repositioning the patient based on images acquired immediately before the treatment delivery is the current standard practice for IGRT. Online repositioning strategies practiced in most clinics so far are limited to correct for translational shifts only, failing to account for rotational errors, volume changes and deformations of targets and OARs, and independent motions between different targets/OARs. This is in spite of the fact that the current technology provides enough information to perform much more detailed modifications to the daily treatment than simple translational shifts. In principle, the data required to generate a new treatment plan for the day is available in today's CT-based IGRT practice, but by using the data only for shifting the patient, the full potential of the IGRT is not exploited.

There has been ongoing research to extend online corrections from the table shifting to modifications that can correct for changing anatomy, such as organ rotations and deformations. For example, correction for rotations in addition to translations has been implemented, at least partially, in several technologies (e.g., Tomotherapy). However, other inter-fraction variations may not accounted for and remain a major concern. Such variations can be handled by online re-planning methods, including rapid online plan modifications and full-blown plan re-optimization based on anatomy of the day. For example, quick adjustment of beam aperture shapes and weights based on the CT of the day (the anatomy of the day) is an online plan modification method facilitated by advances in computer technology, which allows computationally intensive operations to be performed within a reasonable time frame. Other examples include GPU-based full-blown re-optimization and adaptation based on pre-computed plan libraries. Consequently, online correction schemes that are more comprehensive than online repositioning are beginning to move into the clinic. However, such online re-planning approaches still present challenges since they require delineation of targets and OARs, which is time a consuming and difficult process to fully automate. As such, manual delineation, or even manual contour validation, on single or multi-modality imaging is the main bottleneck for an online re-planning process to be performed within a few minutes.

Therefore, given the above, there is a need for systems and methods employing multi-modality images for use in adapting and delivering radiotherapy treatments in clinically feasible time frames.

SUMMARY

The present disclosure overcomes the aforementioned drawbacks by providing systems and methods directed to adaptive radiotherapy planning.

In accordance with one aspect of the disclosure, a system for developing a radiotherapy treatment plan is provided. The system includes a data storage device configured to hold MR image data acquired by an MRI system, and at least one processor configured to receive the MR image data from the data storage device, apply corrections to the MR image data to produce a series of corrected image data, and assemble the series of corrected image data to generate a set of relaxometry maps. The at least one processor is also configured to perform a segmentation of a plurality of regions of interest using the set of relaxometry maps, classify the plurality of regions of interest, using the set of relaxometry maps, to yield a plurality of classified structures, and assign electron density values to the classified structures using an assignment process. The at least one processor is further configured to generate, using the electron density values of the classified structures, a set of corrected synthetic electron density images, and perform a dose calculation using the corrected synthetic electron density images to develop a radiotherapy treatment plan.

In accordance with another aspect of the disclosure, a method for producing synthetic images for use in a radiotherapy treatment is provided. The method includes directing a magnetic resonance imaging (MRI) system to acquire a plurality of image data for use in a radiotherapy process, receiving the plurality of acquired image data from the MRI system, and applying corrections to the MR image data to produce a series of corrected image data. The method also includes assembling the series of corrected image data to generate a set of relaxometry maps, performing a segmentation of a plurality of regions of interest using the set of relaxometry maps, and classifying the plurality of regions of interest, using the set of relaxometry maps, to yield a plurality of classified structures. The method further includes assigning electron density values to the classified structures using an assignment process, generating, using the electron density values of the classified structures, a set of corrected synthetic electron density images, and optionally performing a dose calculation using the corrected synthetic electron density images to develop a radiotherapy treatment plan In accordance with yet another aspect of the disclosure, a method for adapting a radiotherapy treatment plan is provided. The method includes providing an initial radiotherapy plan to be adapted according to an updated image set, the initial radiotherapy plan having a radiation dose distribution, determining a plurality of dose gradients using the radiation dose distribution, and defining an optimization objective using the dose gradients. The method also includes receiving the updated image set, generating, using the updated image set, an updated set of contours representative of an updated target volume, and forming a set of partial rings using the updated set of contours, the set of partial rings arranged about the updated set of contours representative of the updated target volume. The method further includes performing a plan optimization using the optimization objective and the set of partial rings, and generating a report representative of an adapted radiotherapy plan obtained using the plan optimization.

The foregoing and other advantages of the disclosure will appear from the following description.

DETAILED DESCRIPTION

Figure 1:
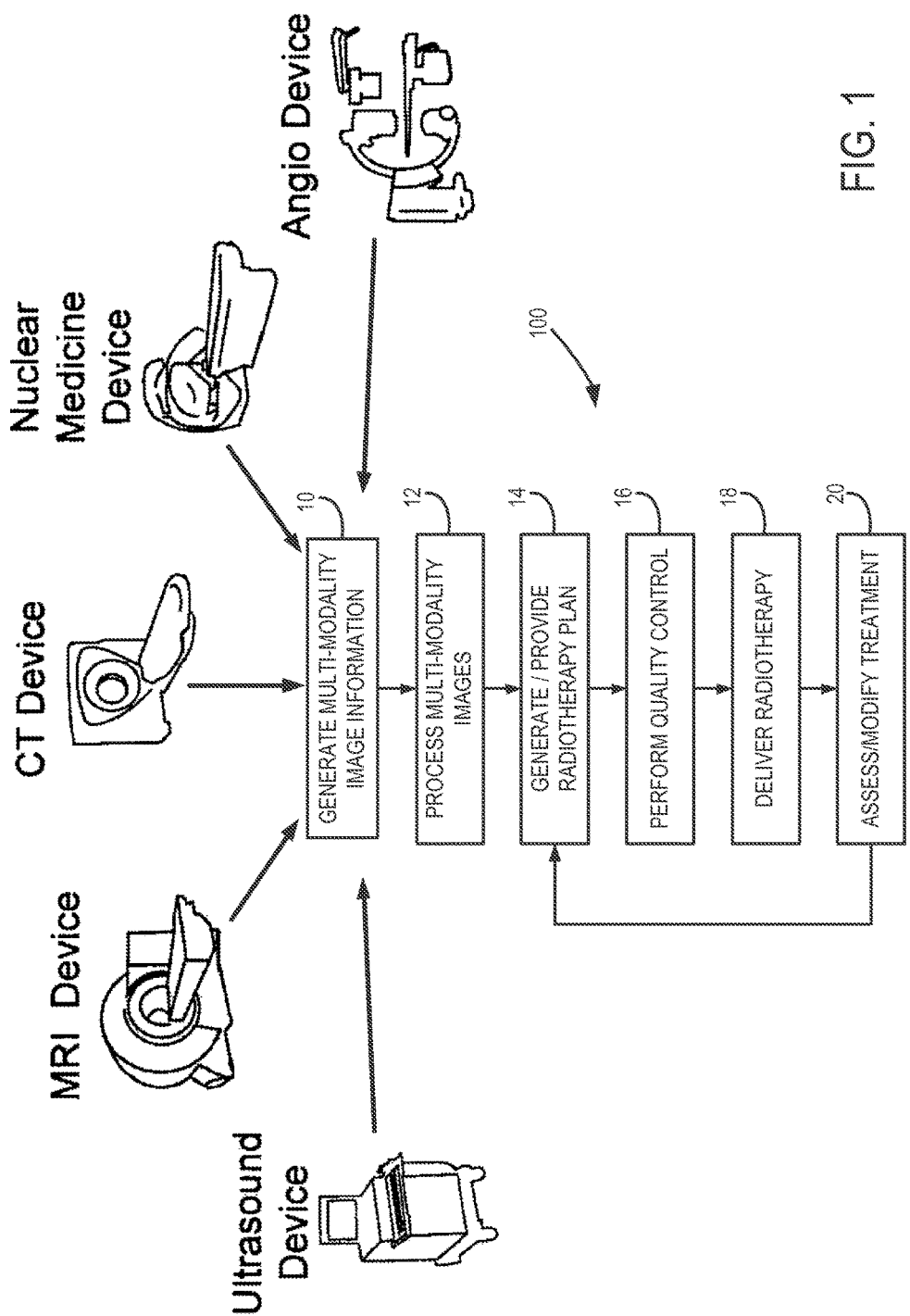
FIG. 1 shows a flowchart setting forth steps associated with the process of providing radiotherapy treatment to a patient.

Current clinical practice associated with delivery of any one or more radiotherapy treatments involves complex, carefully coordinated workflows, employing a multitude of tools and systems designed to achieve maximal patient benefit. FIG. 1 shows an example flowchart illustrating the general steps associated with such a radiotherapy treatment process. The process 100 typically begins at process block 10, where medical image information is generated from a patient typically using of a variety of imaging approaches, either for diagnostic or treatment purposes. For example, as illustrated in FIG. 1, this can include use of computed tomography (CT) devices, magnetic resonance imaging (MRI) devices, positron emission tomography (PET) imaging devices, ultrasound (US) imaging devices, and so forth. Information obtained from imaging serves two main purposes in radiotherapy (RT). First, it is used to determine true three-dimensional positions and extent of targeted diseased tissues relative to adjacent critical structures or objects at risk (OARs), which typically have radiation dose toxicity constraints. Second, it is used to localize such targets and OARs, for example, during a daily treatment setup, in order to make any treatment adjustments prior to radiation delivery.

In general, CT images are the standard imaging modality utilized for treatment planning. In a simulation stage, a patient is immobilized and imaged with reference marks that establish specific coordinates, which may subsequently be reproduced in a treatment system during radiation delivery. The acquired images are then utilized in a planning stage to generate a treatment plan. In addition to CT images, other imaging modalities offer improved contrast and other useful information related to anatomical features and biological processes of normal and diseased tissues or structures. In particular, MRI is non-ionizing, and offers superior soft tissue contrast compared to CT, while providing a wide array of functional contrast forming mechanisms to characterize tumor physiology. However, in contrast to CT images, MR images lack electron density (ED) information, which is necessary for radiation dose calculations. Hence, such non-CT images need to be processed or synthesized to be "CT-like" in order to find use in RT planning and delivery.

Previously, different approaches have been explored to transform MR images into CT-like images, namely: 1) manual bulk electron density assignment, 2) deformable image registration, 3) voxel-based classification, 4) use of ultra-short echo time (UTE) images, and 5) use of Dixon images. Each of these methods has its drawbacks, as described below.

In manual bulk density assignment methods, tissue contours are manually constructed on a patient's MR image and bulk electron densities are then assigned to each of the manually constructed structures. The major issue with this method is that it suffers from large intra- and inter-observer variability. Variability in observer contouring, particularly at tissue interfaces, has been shown to produce severe errors in the computed dose distribution. In deformable image registration (DIR) methods, a vector displacement field (VDF) is typically estimated by warping a patient's MRI image to a reference MRI image. The VDF is then applied to warp a "gold standard" CT image back to the vector space of the patient's MRI image. However, the accuracy of this method is subject to the accuracy of DIR and, particularly, can be challenged in patients with atypical anatomy. In addition, non-uniform MR image intensities, induced by B1+ (RF transmit) and B1− (RF receive) inhomogeneities can challenge the accuracy of intensity-based DIR algorithms. Moreover, variations in grayscale signal intensities, common in conventional, magnitude MR images, can also challenge the accuracy and robustness of intensity based DIR algorithms. In voxel-based classification methods, each voxel is classified into a specific tissue type, followed by direct conversion of MRI gray scale intensities to Hounsfield units or electron densities. However, non-uniform image intensities and variations in conventional magnitude MR image grayscale intensities can again confound the accuracy of tissue classification with voxel-based methods. Although UTE sequences may offer advantages for imaging bone, they lack contrast for other tissue types and are not yet commercially available on all clinical MRI scanners. Finally, misregistration of multi-echo Dixon images can confound image segmentation, resulting in blurred structure boundaries.

In addition to having accurate and usable image information, the present disclosure recognizes that CT-like or CT substitute images need to satisfy some additional conditions to find practical use in RT treatment. Specifically, such images necessitate 3D volumetric coverage composed of contiguous slices to allow for accurate and complete structure delineation for treatment plan evaluation using dose-volume histograms (DVH's). Also, full patient cross-sections within a field of view (FOV) are needed for accurate dose calculation, because such calculations involve distances between a radiation source and a patient's skin. In addition, for accurate treatment verification through improved digitally reconstructed radiograph (DRR) image quality, slices thicknesses of 3 mm or less are advantageous, while accurate image registration and image segmentation algorithms may benefit from high spatial resolution (for example, less than 1 mm$^2$) and image uniformity. With respect to imaging of body regions susceptible to respiratory, peristaltic, and cardiac motion, appropriate acquisition speed is desirable for artifact-free images, while accurate anatomical delineation and dose accumulation calls for high geometric fidelity.

Conditions imposed by the nature of RT treatment have limited use of non-standard images to qualitative assessment. In particular, despite the advantages in soft tissue contrast that MRI provides, drawbacks such as the lack of electron density information, geometric distortion, and signal non-uniformities, have hindered the establishment of MR imaging as a primary imaging modality in RT treatment.

Therefore, it is one aspect of the present disclosure to provide systems and methods that successfully implement non-ionizing MR imaging into a RT treatment process. Specifically, such systems and methods may be used to generate synthetic ED images that overcome shortcomings of prior approaches, and are practical for use in RT treatment planning. As will be described, synthetic ED images may be obtained using relaxometry parameter maps, with the images being fully corrected for known sources of error, including magnetic field (B0) errors, RF transmit field (B1+) inhomogeneity errors, and geometric distortion errors from gradient nonlinearity.

Figure 2:
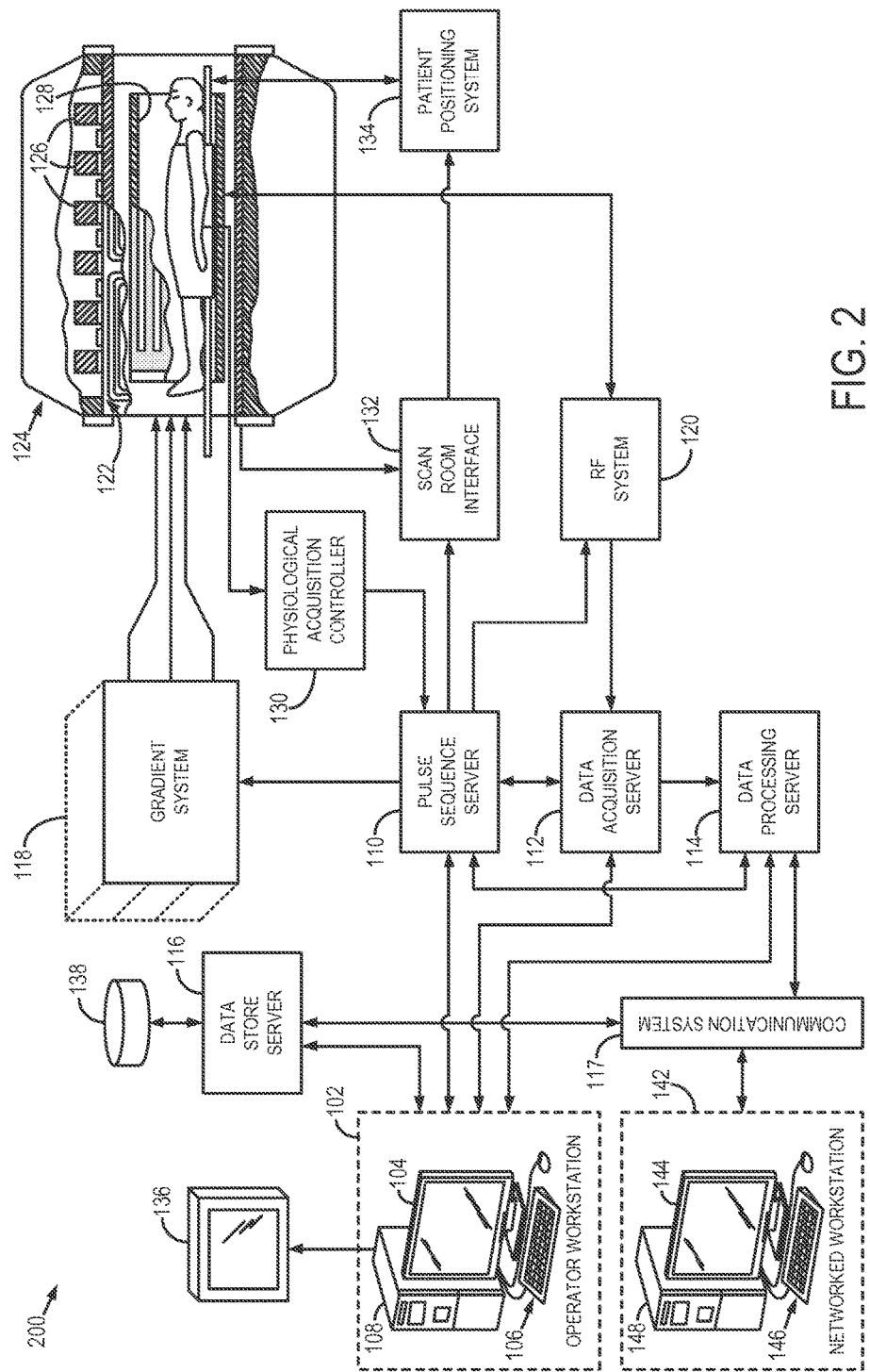
FIG. 2 is a schematic of an example MRI system for use in accordance with the present disclosure.

Referring specifically to FIG. 2, an example of a magnetic resonance imaging (MRI) system 200 is illustrated. The MRI system 200 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 200. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients and used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 2), in order to perform the prescribed magnetic resonance pulse sequence. Responsive magnetic resonance signals detected by the RF coil 128, or a separate local coil (not shown in FIG. 2), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 2).

The RF system 120 also includes one or more RF receiver channels. Each RF receiver channel includes an RF preamplifier that amplifies the magnetic resonance signal received by the coil 128 to which it is connected, and a detector that detects and digitizes the quadrature components of the received magnetic resonance signal. The magnitude of the received magnetic resonance signal may, therefore, be determined at any sampled point by the square root of the sum of the squares of the components:

$$M = \sqrt{I^2 + Q^2} \tag{1};$$

and the phase of the received magnetic resonance signal may also be determined according to the following relationship:

$$\varphi = \tan^{-1}\left(\frac{Q}{I}\right). \tag{2}$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during pre-scans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 200 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Signals acquired using an MRI system 200, as described, unlike CT image signals, bear no direct relationship to electron density. Therefore, in some aspects, MRI system 200, independently or in cooperation with other processing or analysis systems, may be configured to process magnetic resonance data, reconstructed images, and/or other data to generate data, images, or information suitable for use in radiation therapy, as described.

Figure 3:
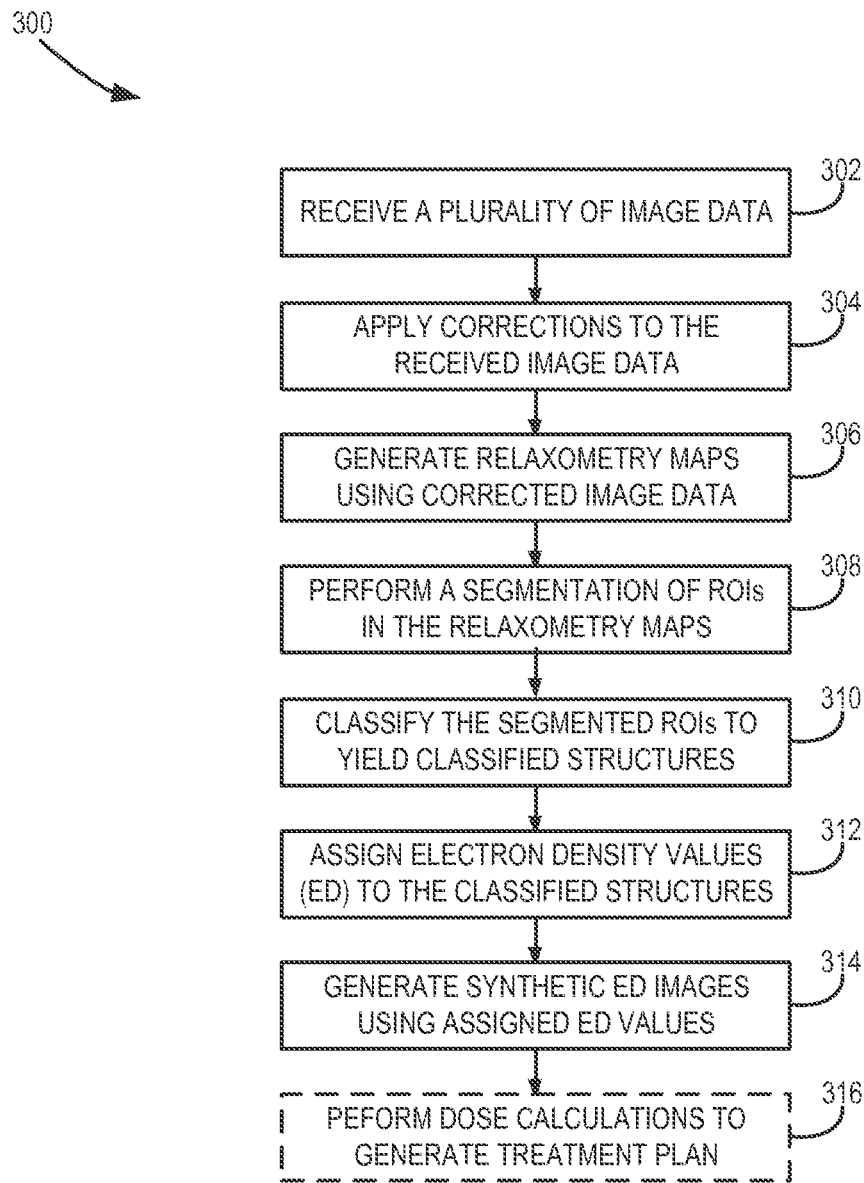
FIG. 3 is a flowchart setting forth steps associated with operation of the MRI system of FIG. 2 to generate synthetic electron density images, in accordance with the present disclosure.

Referring now to FIG. 3, a flowchart is shown setting forth steps of a process 300 for generating synthetic ED images, in accordance with aspects of the present disclosure. In particular, steps of process 300 may be carried out using a number of suitable systems or devices, including imaging systems, planning systems, processing systems, and so on, or combinations thereof.

Specifically, process 300 may begin at process block 302 whereby a plurality of image data is received, for example from a data storage, or other computer readable medium, wherein the image data includes 1D, 2D, 3D, and 4D image data. In some aspects, process block 302 may include directing a MRI system, as described, to acquire a plurality of image data for use in a radiotherapy process, and receiving the acquired image data therefrom. By way of example, received or acquired images, can include 3D fast low angle shot (FLASH) images using multiple flip angles, 3D balanced steady-state free precession (bSSFP) images using multiple flip angles, 3D GRE images using multiple echo times, 3D actual flip angle (AFI) images using multiple repetition times (TR's), and so forth. As described, acquired images may need to include the volumetric coverage, slice thickness, spatial resolution, geometric fidelity, and image uniformity suitable for use in radiotherapy process. In addition, with respect body regions susceptible to motion, appropriate acquisition speed and/or motion corrections may be needed for obtaining artifact-free images and hence accurate treatment plans. In accordance with some aspects of the disclosure, a retrospective temporal reshuffling of k-space data may be utilized to generate phase resolved 4D MR image data, as will be described.

At process block 304, a number of corrections may be applied to the received or acquired image data, as discussed below.

In particular, 3D gradient nonlinearity geometric distortion corrections may be applied to any or all images by applying various correction algorithms. In some preferred aspects, such corrections may be performed using a vector deformation field (VDF) established by comparing reversed gradient images of a distortion phantom, whereby the phantom's design images may be employed on a scanner-by-scanner basis. This approach is more robust than the Legendre polynomial 3D distortion correction algorithm provided by the scanner manufacturer, after which residual geometric distortions often remain.

Also, corrections may be performed to account for off-resonance effects, including main field (B0) inhomogeneity, chemical shift, and magnetic susceptibility effects. In particular, these may be corrected by generating magnetic field maps of the patient determined with phase difference mapping based on 3D gradient-recalled echo (GRE) images obtained at two echo times. In some aspects, the GRE images used to generate the magnetic field maps may be a subset of the multi-echo GRE images used for T2* mapping discussed below, thereby increasing scanning efficiency.

In addition, any or all images may be corrected for RF transmit/receive field inhomogeneities. Specifically, rapid mapping of the B1+(RF transmit field) may also be performed using the actual flip angle imaging (AFI) imaging method, which consists of a modified 3D FLASH sequence with two repetition times, large spoiler gradients, and a specific RF phase cycling schedule. A 2nd to 7th order polynomial surface may then be then fit to smooth the resulting flip angle (FA) maps, which are directly related to the B1+ field. In addition, correction for B1– (RF receive field) may also be performed using phased-array coil sensitivities measured immediately prior to data acquisition, for example, using a pre-scan.

At process block 314, a number of relaxometry maps are generated by assembling the corrected image data, including T1, T2, and T2* maps. Specifically, a rapid T1 mapping may be performed using a set of several 3D FLASH images (e.g. 3 to 5) acquired with different flip angles, for example, 2, 5, 10, 15, 25 degrees, although other values are possible. As described, images may be corrected for gradient nonlinearities and off-resonance induced spatial distortions. A "flip angle series" may be formed and a T1 parameter map may be obtained by a least squares fitting of the flip angle series to the corrected flip angles, determined using the B1+ map. Also, rapid T2 mapping may also be performed using the set of several 3D balanced bSSFP images acquired with different flip angles. Each of the multiple flip angle images may be corrected for gradient nonlinearities and off-resonance induced spatial distortions. A flip angle series may be formed and a T2 parameter map may be obtained by least squares fitting of the flip angle series to the corrected flip angles, determined using the B1+ map, as well as T1 and B0 parameter maps. Furthermore, T2* mapping may further be performed using acquired 3D multi-echo GRE images, using, for example, a set of four to eight echo times, with an "echo series" of phase corrected real images being outputted. Echo times may be in the range of 0.07 to 30 ms, although other values are possible. As described, images may be corrected for gradient nonlinearities and off-resonance induced spatial distortions. A T2* parameter map may then be obtained by least squares fitting of the phase corrected real images to echo times.

Figure 4:
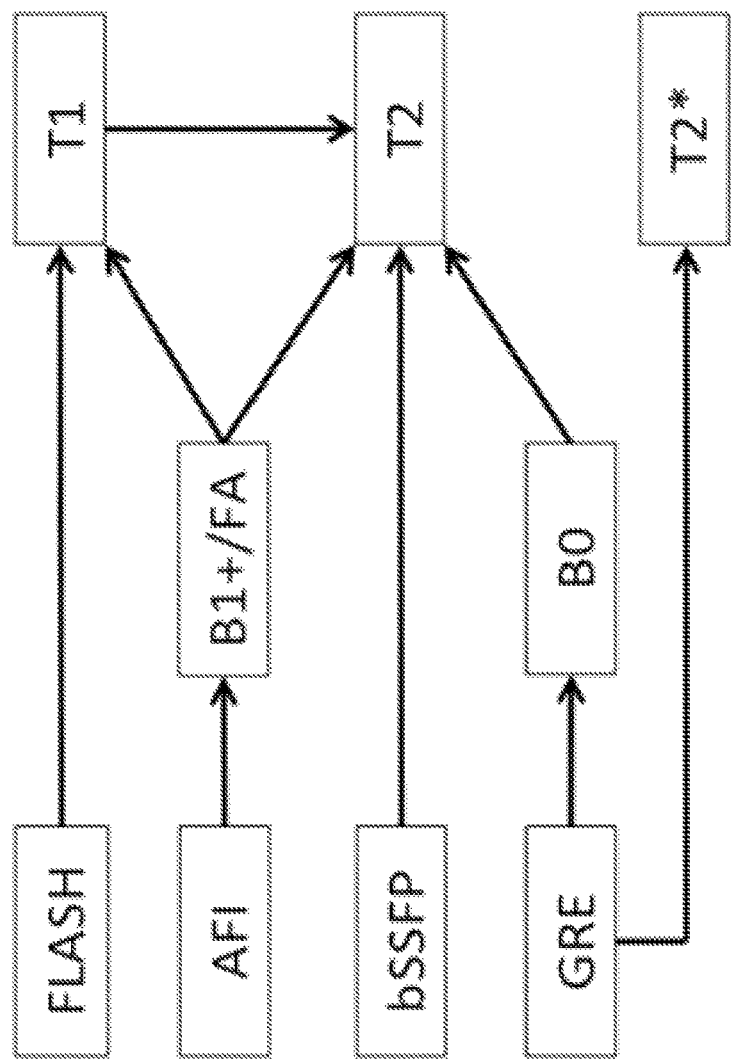
FIG. 4 is a block diagram of an example image acquisition and post-processing using the system of FIG. 2, in accordance with the present disclosure.
Figure 5:
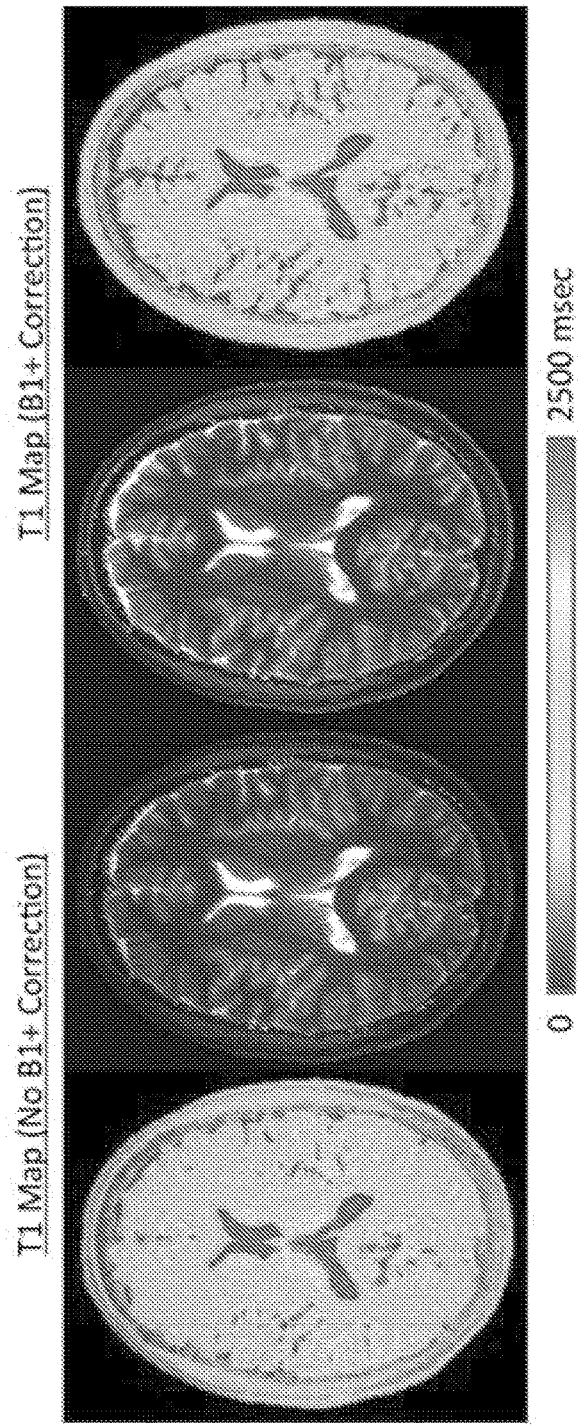
FIG. 5 shows an example of brain T1 parameter maps from a healthy volunteer generated with and without B1+ correction, in accordance with the present disclosure.

A block diagram representing an example image acquisition and post-processing steps, as described, is shown in FIG. 4. By way of example, illustrating the effects of B1+ inhomogeneities on T1 parameter maps, FIG. 5 compares corrected and uncorrected brain images from a healthy volunteer. Without correction for B1+ inhomogeneity, T1 maps show considerable non-uniform image intensities (shading), as demonstrated in the grayscale and color maps on the left of FIG. 5. The shading translates into errors in the calculated T1 relaxometry values, which must be corrected for accurate tissue segmentations. Applying the B1+ correction results in highly uniform T1 parameter maps, as shown in the grayscale and color maps on the right side of FIG. 5. Similar results were obtained for T2 parameter maps.

Referring again to FIG. 3, at process block 308, relaxometry maps and other images generated based on corrected image data, as described above, may be segmented according to specific regions of interest (ROIs). For instance, a segmentation may be performed by thresholding MR relaxometry parameters. In some aspects, the segmentation may be implemented using Otsu's method, an approach that applies clustering-based image thresholding, with T1, T2, and T2* values used as inputs. Other image segmentation approaches may also be used, automated or semi-automated techniques.

Figure 21:
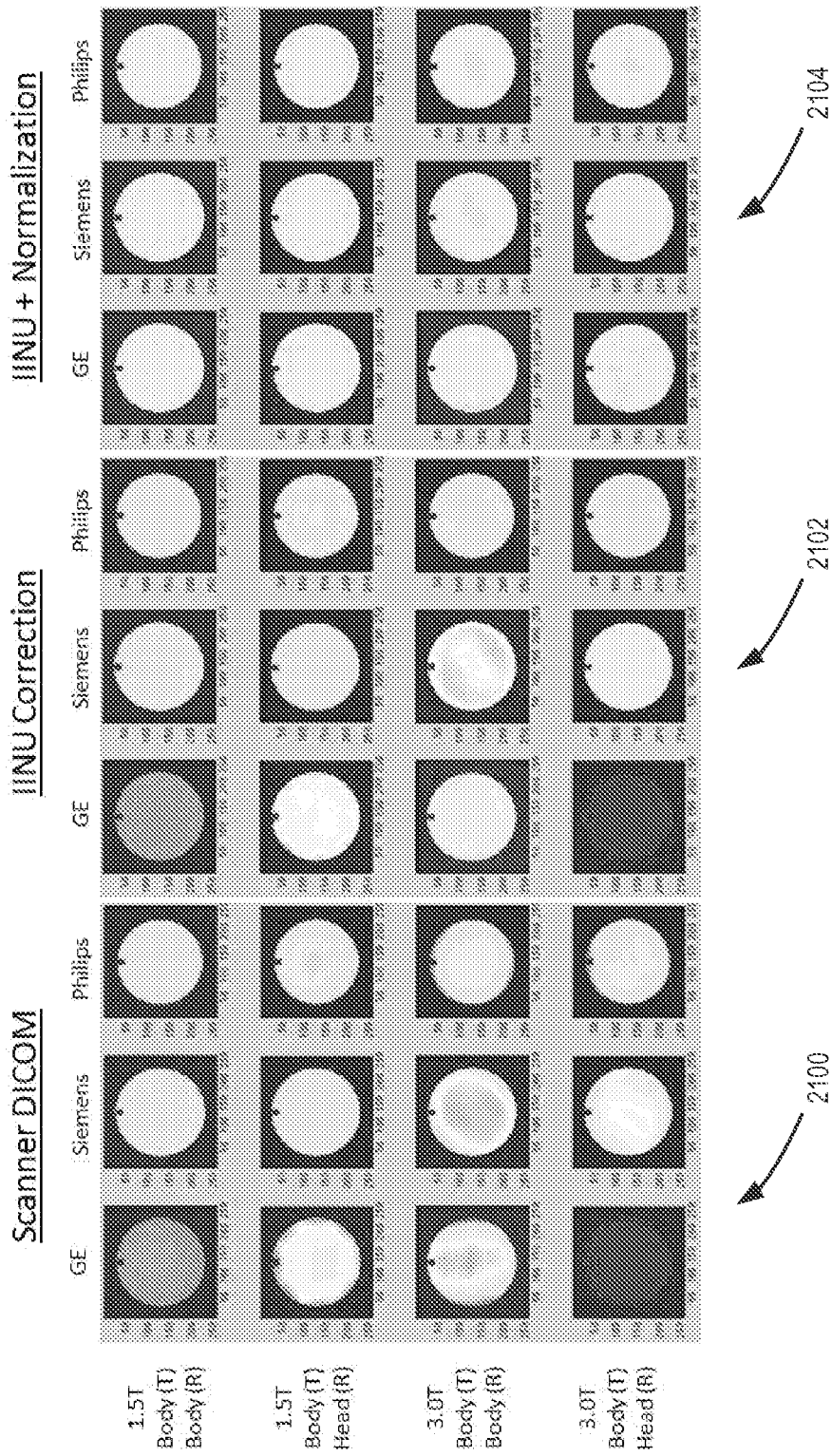
FIG. 21 shows a comparison between image intensities obtained using various MRI scanners and scanning conditions, and subject to corrections and normalization, in accordance with aspects the present disclosure.

As illustrated in the example of FIG. 21, MR scanners from various manufacturers produce images that can vary not only in homogeneity, as described, but may also differ in overall intensities levels, as generally indicated by 2100. Although corrections for off-resonance effects, gradient inhomogeneity and other artifacts may be corrected as described, such corrections do not affect the overall intensity levels, as shown by 2102. As such, in some aspects, images or maps may also be corrected for intensity variation by performing a normalization procedure. This may include receiving an indication of the scanner type, or manufacturer, and imaging conditions, such as magnetic field strength, and applying a normalization in accordance with the received indication. As indicated by 2104, such normalization can achieve a standardization of images across manufacturers and imaging conditions, fixing window widths and levels in a manner that may be advantageously used during segmentation and position verification.

At process block 310, a tissue classification of ROIs segmented at process block 308 may be performed according to image intensities appearing the set of relaxometry maps. For example, an atlas-based tissue classification may be utilized. Specifically, segmented structures or organs may be classified according published MR relaxometry values (for example, T1, T2 and T2* relaxation times) acquired at a given magnetic field strength, such as, 3 Tesla.

Then, at process block 312, electron density values may be assigned to the classified structures using an assignment process. In particular, structures or organs classified at process block 308 may be assigned tissue-specific electron density values. Such ED values may determined, or computed in any manner, or otherwise obtained from any reference, such as ICRU Report #46.

Figure 6:
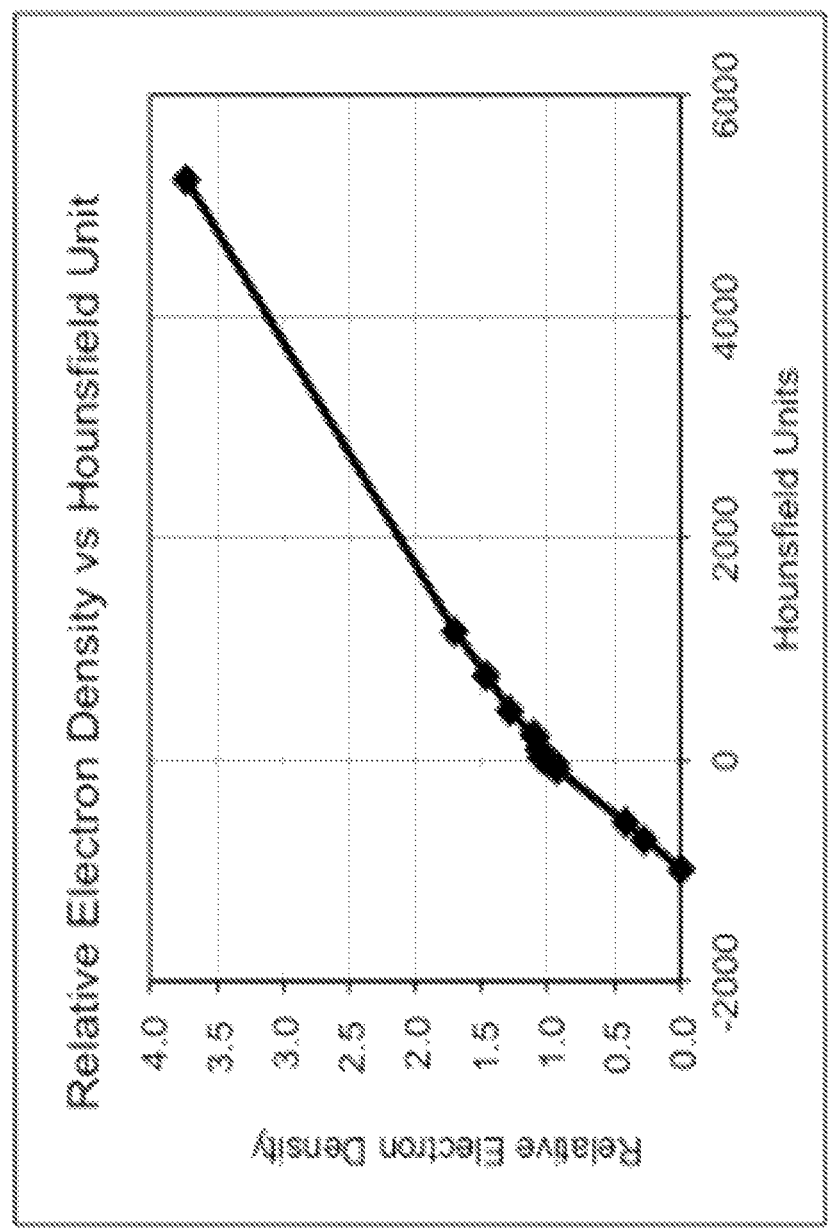
FIG. 6 is a graphical illustration of electron density to Hounsfield Unit conversion table from clinical radiation treatment planning system used to convert synthetic electron density image to synthetic CT image, in accordance with the present disclosure.

At process block 314, synthetic electron density image images, for example, in the form of a 3D or 4D image set and corrected for distortions and inhomogeneties, as described, may then be generated using the classified structures. In some aspects, corrected synthetic electron density images may be converted to synthetic CT images, for example, by utilizing an inverted CT-ED standard conversion table, generally available on clinical radiation treatment planning systems. FIG. 6 shows a graph illustrating a conversion between relative electron density and Hounsfield units (CT number).

Electron density values associated with the corrected synthetic ED or CT images may allow any system, configured for radiotherapy plan development or capable of performing dose calculations using electron density data, to generate treatment plans, as indicated by process block 316. Such dose calculations help to determine a radiation dose distribution, representative of dose received within, around, or generally about, any desired or target regions of interest. In some aspects, dose distributions may be then used or modified in an online radiotherapy plan adaptation strategy, as will be described.

Figure 7:
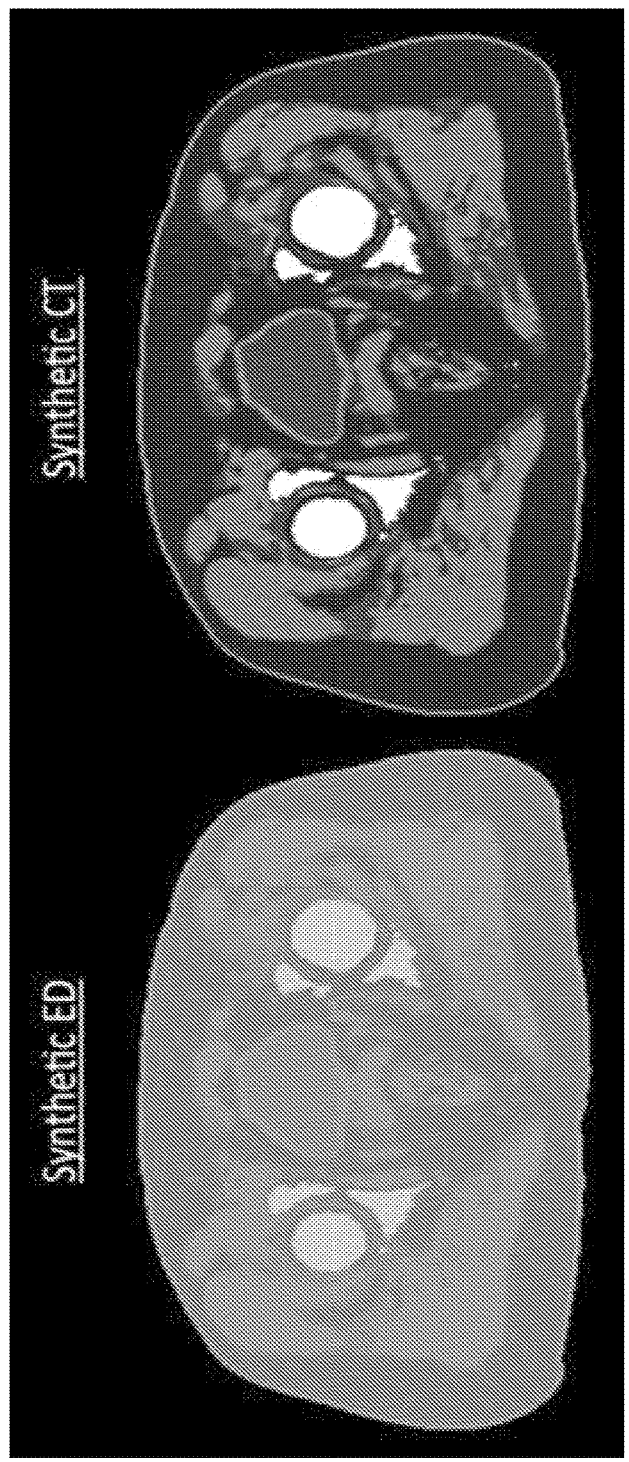
FIG. 7 shows example synthetic electron density and synthetic CT images obtained from the pelvis of a healthy volunteer, in accordance with the present disclosure.
Figure 8:
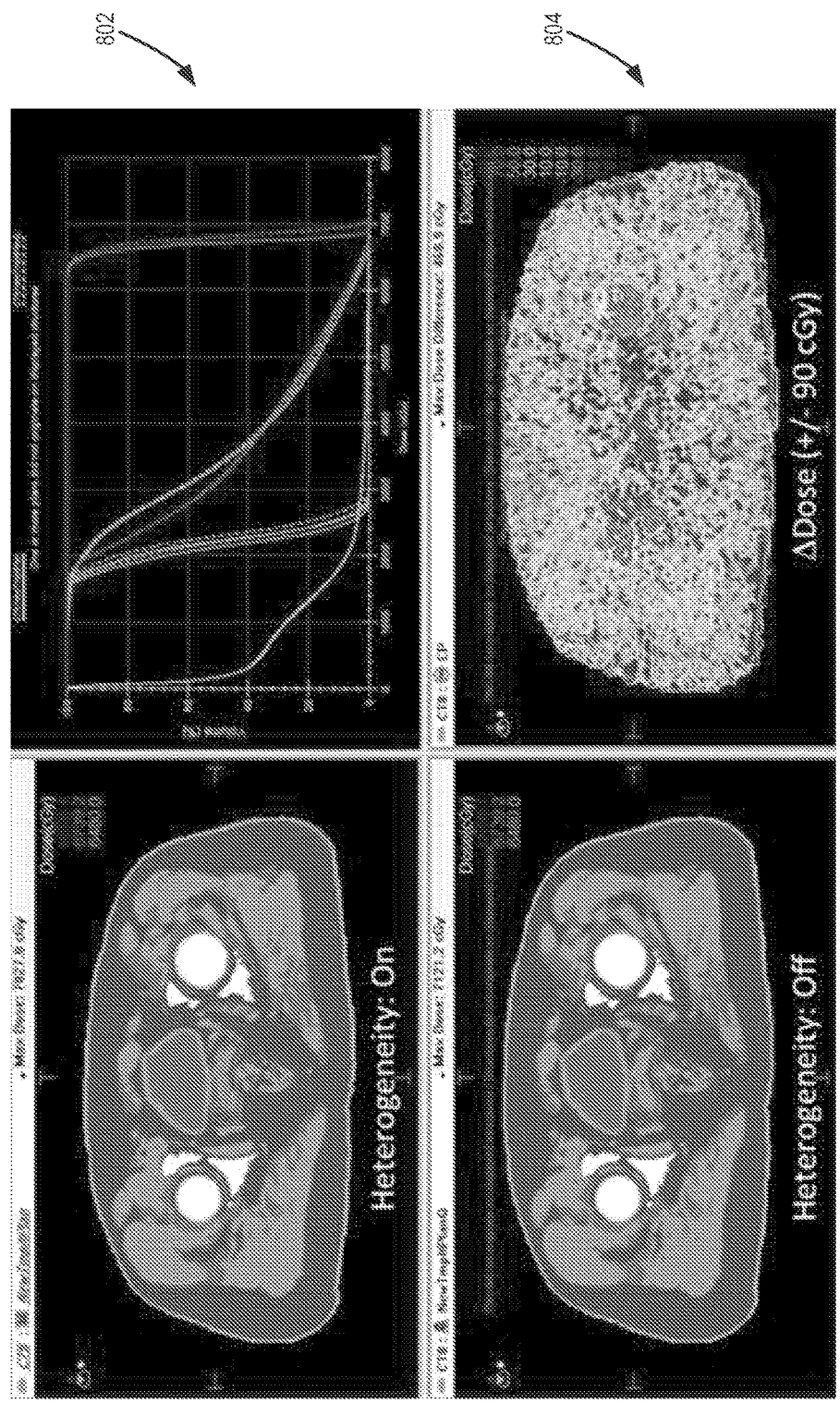
FIG. 8 shows an example volume-modulated arc therapy plan calculated using synthetic CT images with and without heterogeneity corrections, in accordance with the present disclosure.

By way of example, FIG. 7 displays synthetic ED (left) and synthetic CT (right) images of a pelvis for a healthy volunteer, generated according to the aforementioned description. Six tissue types were segmented and assigned electron densities: air, bone, fat, muscle, water (urine in bladder), and skin. Additional tissue classifications (for example, separating cortical bone from bone marrow) beyond that shown in FIG. 7 may still be possible. The pelvic synthetic CT images displayed in FIG. 7 were transferred and loaded onto a Monaco treatment planning system (Elekta, Sweden), where a volumetric modulated arc therapy (VMAT) plan was calculated with and without heterogeneity corrections turned on, as shown in FIG. 8. Differences visible between the solid and dashed lines in the DVH graph shown in the upper right, 802, of FIG. 8, as well as the +/−90 cGy dose difference shown in the lower right, 804, of FIG. 8, demonstrate that the planning system utilized was able to use the information provided by the synthetic CT images to calculate dose with heterogeneity corrections turned on.

The above-described process demonstrates a model-independent, MRI-scanner-independent methodology for synthesizing electron density information from MR image data suitable for use in radiation therapy planning and delivery. The relaxometry parameter maps from which synthetic electron density and synthetic CT images may be derived, are fully corrected for known sources of spatial distortion, non-uniform image intensities and variations in grayscale signal intensities, commonly experienced in conventional magnitude MR images. These features in particular resolve current roadblocks precluding the routine use of conventional magnitude MR images in MR-based radiotherapy and adaptive radiotherapy applications. In addition, the acquisition of the underlying images, from which the synthetic electron density and synthetic CT images are obtained, are fast enough to be performed in breath holds, permitting generation of synthetic CT images in the challenging body regions prone to motion artifacts. Although the described approach does not rely on anatomical models (atlases) or deformable registration, these could be used in conjunction with systems and methods of the present disclosure, if so desired.

As may be appreciated, knowledge of target and organ at risk motion trajectories is critical in radiation therapy. Motion can result in a smearing of planned dose distributions, particularly when steep dose gradients are employed to reduce doses to proximal OARs. A number of strategies have been introduced to manage motion. However, in general, these methods suffer from one or more of the following deficiencies: use of motion surrogates (e.g., bellows, reflector camera, body surface area), invasive implantation of RF transponders, use of ionizing radiation, poor soft tissue contrast, finite penetration depth, lack of temporally correlated spatial information, large irradiated volumes resulting from large margins, diminished treatment efficiency resulting from gating.

Due to its non-ionizing and high soft tissue contrast properties, MR imaging represents an ideal four-dimensional (4D) imaging platform. However, spatio-temporal-contrast resolution tradeoffs preclude acquisition of true, 4D MR images. For instance, the mean, human respiratory period is approximately five seconds. In order to resolve motion similarly to 4D-CT (in which the respiratory cycle is decimated into 10 phases), the ideal 4D-MRI method would need to acquire an artifact-free, high-contrast, high-resolution 3D volume every 0.5 seconds or less. Even with the latest MRI technology, including parallel imaging, multi-band excitation, and compressed sensing, this requirement is still not achievable. Furthermore, the introduction of MR-guided RT places additional demands on fast, volumetric MR imaging. Exception gating and real-time tumor tracking necessitate low latencies in the image acquisition, reconstruction, and segmentation chain.

Therefore, in accordance with aspects of the present disclosure, true 4D-MR images for use in RT treatment may be obtained by performing a retrospective temporal reshuffling of k-space data acquired while patients breathe normally. This approach does not rely on external respiratory surrogates (bellows, reflector camera, body surface area, etc), improves image contrast, and eliminates imaging radiation dose.

By way of example, a data acquisition is described herein. In particular, a golden angle radial pulse sequence may be utilized capable of switching between 2D and 3D cine modes of either balanced steady state free precession (bSSFP) or spoiled gradient recalled echo (SPGR) acquisitions. The DC signal from each acquired radial spoke may be used as a navigator, providing a respiratory surrogate to guide phase-resolved image reconstruction. De-rated maximum gradient amplitudes and slew rates may be used to minimize eddy current effects.

Coronal 4D-MR images, for example may be collected with the sequence running in 3D cine mode with the following parameters: FOV=380 cm, TE=0.8 msec and TR=1.9 msec, As described, a total scan time can be about six minutes. Although, a particular scan implementation has been described above, one skilled in the art will appreciate that various modifications to scan parameters may be performed and considered within the scope of the present disclosure.

Figure 22:
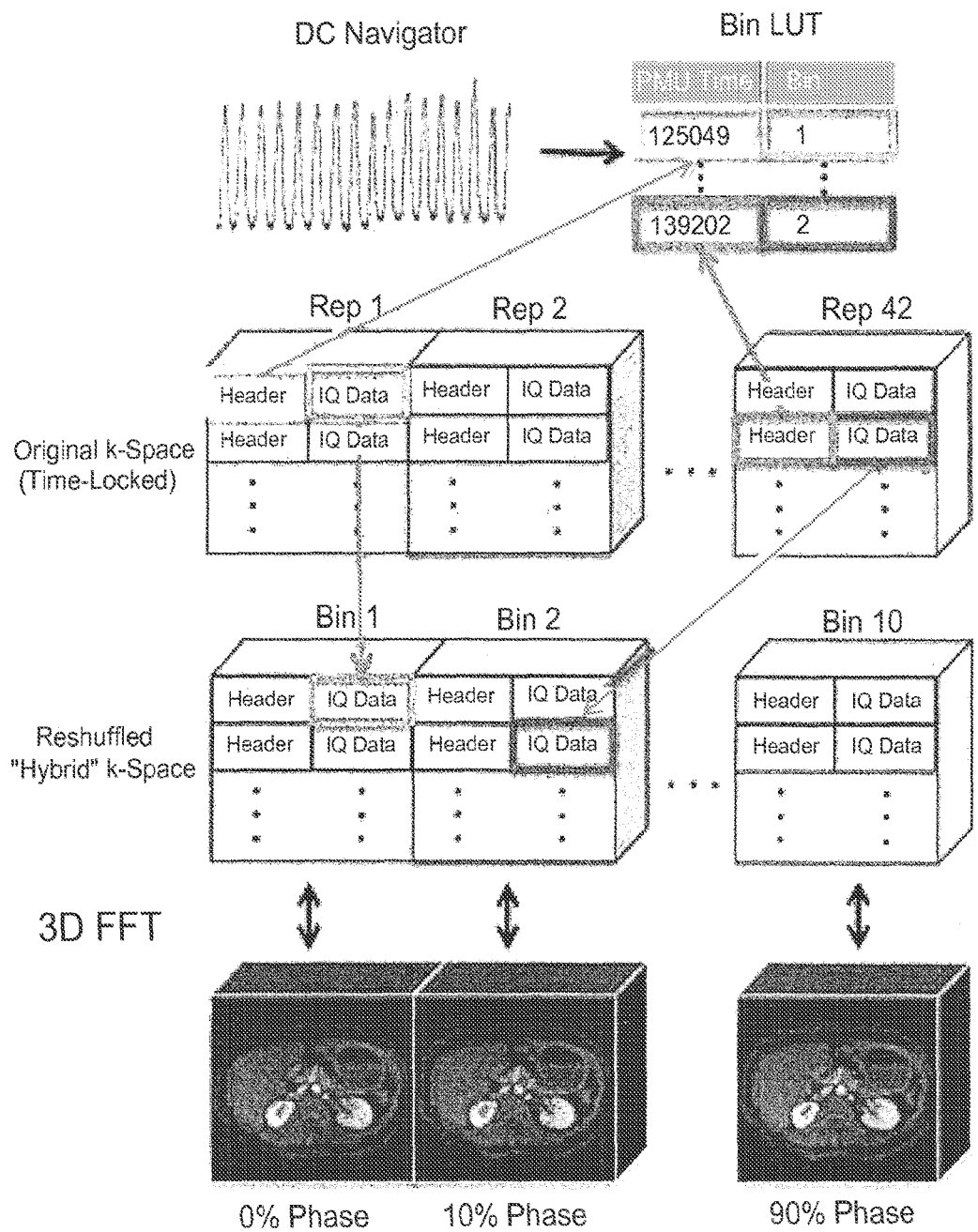
FIG. 22 shows a diagram for a retrospective reconstruction of phase-resolved 4D MR images in accordance with aspects of the present disclosure.

Images based on acquired data, as described, may then be reconstructed using the method illustrated in FIG. 22. In some aspects, raw k-space data may be transferred and processed offline any systems suitable. The DC navigator signal for each radial spoke (or phase encode line) may be determined, and plotted over time, as shown in FIG. 22. A lookup table of bin start times may be generated by decimating each respiratory cycle, obtained from the navigator waveform, into say 10 temporal bins (phases), based either on amplitude or phase. The lookup table of bin start times may then be used to reshuffle the raw 4D-MRI k-space into say a 10-bin (10 phase) hybrid k-space, using the time stamps in the headers of each acquired radial spoke (or phase encode line) or knowledge of the pulse sequence looping structure. Spokes or lines reshuffled to the same location in hybrid space may then be linearly combined, with weighting based on temporal proximity to the center of the bin. Missing lines following the reshuffling may be filled using compressed sensing reconstruction. A 3D FFT may then be applied to convert the reshuffled hybrid k-space data to images for each bin (e.g., 0%, 10%, 20%, etc). The final images for each temporal phase may then be interpolated to a resolution of say 1 to 2 mm$^3$ and converted to DICOM for subsequent image processing. As described, such images may be utilized to obtain synthetic ED or CT images at each phase of the respiratory cycle.

The above acquisition describes a switchable spoiled or balanced sequence. This facilitates certain tumors being better visualized with T1 contrast, as opposed to mixed T2/T1 contrast. Furthermore, for tumors and tissue with slow kinetics (e.g., washout), target visualization on the 4D data can be improved by acquiring the 4D data post-gadolinium. For example, visualization of hepatocellular carcinoma (HCC) and esophageal cancer would benefit from T2/T1 contrast obtained using the bSSFP sequence. However, visualization of liver metastasis would benefit from T1 contrast obtained using the SPGR sequence at a delay following contrast administration. Visualization of lung lesions would benefit from SPGR acquisition through reduced banding artifacts.

In addition, acquiring a DC navigator during 2D cine imaging is a novel approach, which combines the advantages of pencil beam navigators and rapid cine imaging. Similar to pencil beam navigators, extremely low latency are acquired (image reconstruction is not required). This provides information from a pencil beam navigator simultaneously with imaging. Also, the DC navigators are obtained with each phase encode and do not require image reconstruction. This has advantages for MRI-gRT, in that the DC navigator, acquired for each phase encode line, has extremely low latency, and could be used in real-time tumor tracking prediction algorithms to drive the system of multi-leaf collimators (MLCs).

In some aspects, a motion analysis may be performed using images obtained as described above. For instance, respiratory phase images of each 4D-MRI dataset may be analyzed to determine a motion. For example, gross target volumes (GTV)s may be contoured on the first temporal phase and then propagated to the other nine temporal phases using a deformable image registration process. The procedure may also be repeated for other structures or organs, organs at risk, and so on. Using the center of mass (COM) components along each Cartesian axis for each of the contoured structures a principal component analysis (PCA) may be performed to determine the eigenvectors and eigenvalues of GTV and structure COM motion. Such motion analysis may be useful for implementation during RT treatment delivery, as will be described.

Synthetic CT images generated using systems and methods, as described, exhibit several advantageous features for MRI-based radiation therapy compared to other alternatives, including, full compatibility with existing kilovoltage (kV) and megavoltage (MV) CT-based IGRT techniques, full compatibility with rapidly developing MRI-based IGRT technologies, and full compatibility with MRI or CT-based adaptive radiotherapy, that account for daily changes in the position, size, and shape of tumor and critical structures, and permit additional reduction of margin size. Additionally, in some envisioned aspects, application of the above-described methodology may be extended to proton-based radiation treatment planning and delivery methods, as well as, systems and applications requiring attenuation correction of positron emission tomography (PET) images, such as combined PET/MRI scanners.

Turning back to FIG. 1, at process block 12 any multi-modality image information acquired, such as described above, or in any other way, may be processed or analyzed using any desired systems and methods to yield image information for use in treatment plan generation and delivery. As will be described, post-acquisition processing of images may involve any number of steps or approaches. For example, these can be providing corrections for known sources of noise, or applying various image transformation, deformation, or registration algorithms, or determining optimal display characteristics to facilitate accurate identification of anatomical structures (for example, widow or level), or delineating objects of interest, or generating synthetic images, to name but a few.

Many commercial systems in use today are capable of generating multi-modality image data captured contemporaneously, such as using CT/MRI, PET/CT or PET/MRI systems. However, in many cases, such systems are either not available or not part of the clinical workflow practice for radiation therapy. Thus, typically, at process block 12 separately acquired multi-modality images may need to be combined to provide complementary information requisite for accurate determination of critical objects. Since typically such images are acquired using different scanners, and usually at different times, transformation, or registration, as is known in the art, is required for images or contoured structures in different sets of data to occupy the same coordinate system. Simply, the process of image registration involves determining a geometrical transformation that aligns points in one view of an object with corresponding points in another view of that object or another object, where the view may be a two- or three-dimensional view, or the physical arrangement of an object in space.

Figure 9:
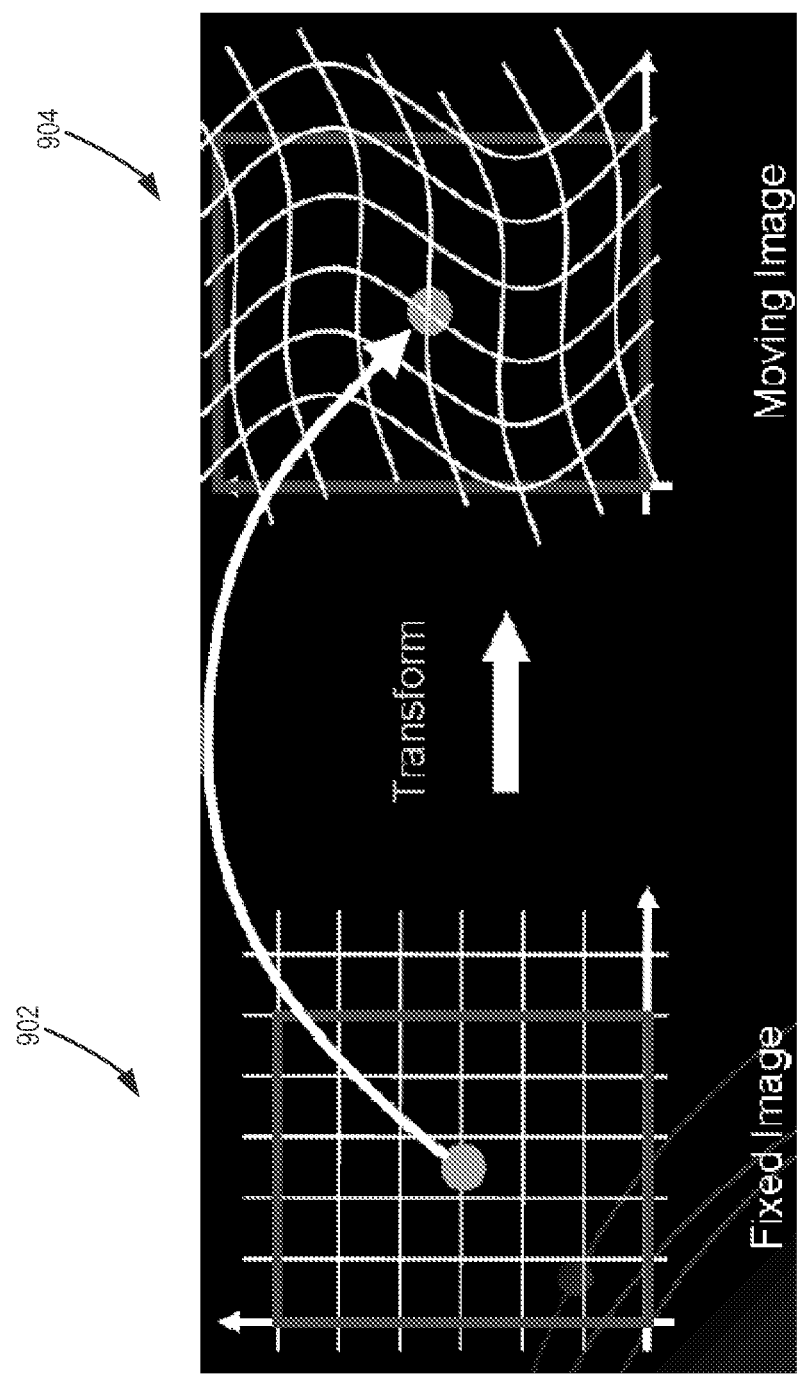
FIG. 9 shows an illustration of a deformable transformation between a fixed and moving image, in accordance with the present disclosure.

Image registration typically involves inter-modality images, such as CT and MR images, MRI and PET images, PET and CT images, contrast-enhanced CT images and non-contrast-enhanced CT images, ultrasound and CT images, and so on. In addition, image registration may also be used for intra-modality imaging, wherein structures may be shifted or distorted between image sequences acquired at different times. FIG. 9 illustrates an example of a registration between a fixed image 902 and moving image 904. Therefore, in the context of adaptive radiotherapy, it may desirable to adjust or modify images or contours of targets and/or critical structures, identified and employed at an initial radiation therapy planning stage, according to daily or current imaging, whose volumes or shapes may have changed above a desired threshold.

Among the many free form registration approaches, the parameterized b-spline deformable image registration (DIR) method has the benefit of automation efficacy, local deformation control and multi-modality capability. However, the deformation pattern of the model does not necessarily follow the real movement of the organs due to lack of physical model support, and therefore induces artifacts such as bone warping and inaccurate fine structure correspondence. Thus, alternative image registration approaches, that are more accurate, are desirable.

In one aspect of the present disclosure, a new registration method is provided, designed to mitigate the drawbacks of previous methods. In particular, a modified parameterized b-spline deformation model may be utilized, designed to overcome previous limitations by using a new regularization method, namely bending energy limited diffeomorphism (BELD). Diffeomorphism regularization is typically used to guarantee the deformation smoothness, and is computationally costly due to Jacobian matrix calculation of all grid points in every iteration step. However, diffeomorphism regularized result does not necessarily follow the real deformation path. Thus, in the present disclosure, accurate diffeomorphism is achieved by limiting the difference between adjacent grid deformation parameters, instead of computing heavily the Jacobean matrix as is common in traditional approaches. The bending energy penalty may be further used to limit the freedom of smoothness, preserving structure topology, and increasing the registration accuracy. Thus, the bending energy penalty in different parts of the images can then be differentiated conveniently through auto-segmentation of major components (bone, body liquid, tissue and air) of both target and source images.

In particular, the bending energy may be used as a penalty term in B-spline deformation mode, calculated as follows:

$$E_B \sum_{\vec{r}} \left(\frac{\partial^2 T_{\vec{r}}}{\partial x^2}\right)^2 + \left(\frac{\partial^2 T_{\vec{r}}}{\partial y^2}\right)^2 + \left(\frac{\partial^2 T_{\vec{r}}}{\partial z^2}\right)^2 + 2\left[\left(\frac{\partial^2 T_{\vec{r}}}{\partial x \partial y}\right)^2 + \left(\frac{\partial^2 T_{\vec{r}}}{\partial y \partial z}\right)^2 + \left(\frac{\partial^2 T_{\vec{r}}}{\partial z \partial x}\right)^2\right] = 0, \quad (3)$$

where $T(\vec{r})$ is the local transformation at location $\vec{r}$. This term is computationally costly when soft tissue makes up the majority part in the region of interest. If the B-spline transformation is written in the tensor product form $$d^l(\vec{r}) = \sum_{i,j,k} c^l_{i,j,k} \beta^n\left(\frac{x}{m_x} - i\right)\beta^n\left(\frac{y}{m_y} - j\right)\beta^n\left(\frac{z}{m_z} - k\right) \quad (4)$$

where $l \in \{x, y, z\}$ and $\beta^n$ is a nth order B-spline basis, the penalty function from is defined as $$p(t) = \begin{cases} \frac{1}{2}(t + \zeta_1)^2, & t \leq -\zeta_1 \\ 0, & -\zeta_1 < t \leq -\zeta_2 \\ \frac{1}{2}(t + \zeta_2)^2, & \text{otherwise} \end{cases} \quad (5)$$

where the argument t denotes a difference between two adjacent deformation coefficients. When combined with B-spline coefficient, the penalty function is $$R(c) = \sum_{l \in \{x,y,z\}} \sum_{i,j,k} \{p_x^l(c_{i+1,j,k}^l - c_{i,j,k}^l) + p_y^l(c_{i,j+1,k}^l - c_{i,j,k}^l) + p_z^l(c_{i,j,k+1}^l - c_{i,j,k}^l)\}, \quad (6)$$

where $\zeta_1=0$ and $\zeta_2=0$ would correspond to the volume preserving constraint $\det J_T(\vec{r})=1$ for any $\vec{r}$.

Diffeomorphism can be guaranteed using the above method, but within this constraint the deformation still has infinite freedom, while a better solution would satisfy a minimized bending energy requirement. In the BELD approach, instead of building sophisticated reality models, a simplified semi-physical model may be used, where diffeomorphism is limited by minimizing the bending energy at grid points, which is much computationally lighter. With regularization from rigidity map $M(\vec{r})$, BELD constrain and feature point distance, the overall penalty function becomes $$\gamma_1 M(\vec{r}) f(T_{\vec{r}}) + \gamma_2 R(c) + \gamma_3 \sum_{m \neq n} (\vec{r}_m - \vec{r}_n)^2 + \gamma_4 E_B \quad (7)$$

where $\vec{r}_m$ and $\vec{r}_n$ are physical coordinates of corresponding feature points, $\gamma_i$ are empirically determined weighting factors. Although the four extra penalty terms may appear to increase the computational complexity, each term is effective only in limited regions, and hence can be optimized in consecutive stages. Also, due to the nonlinearity nature of the penalty function and mutual information metric, a non-linear conjugated gradient optimization method can be utilized. The search direction may be defined as a linear combination of the cost function gradient and the previous search direction.

In some configurations, the deformable registration method, as described, may be implemented as a software tool, either integrated or in conjunction with any radiation planning systems, image analysis or processing systems and software. Such tool may include a variety of steps and functionalities, such as, for example, the capability to (1) accept input of images of different modalities, (2) convert existing contours on any reference images (e.g., MRI) into delineated volumes and adjust image intensity within volumes to match target images (e.g., CT) intensity distribution for enhanced similarity metric, (3) register reference and target images using an appropriate deformable registration algorithms, as described, (e.g., b-spline, Demons) and generate deformed contours, (4) map deformed volumes on target images, calculate mean, variance, and center of mass as the initialization parameters for consecutive fuzzy connectedness (FC) image segmentation on target image, (5) generate affinity map from FC, (6) generate contours by modifying the deformed contours using the affinity map with a gradient distance weighting algorithm. In addition, such software tool may benefit from GPU processing, which may be orders of magnitude faster than using CPU processing, on account of a highly parallel and efficient processing structure.

Figure 10:
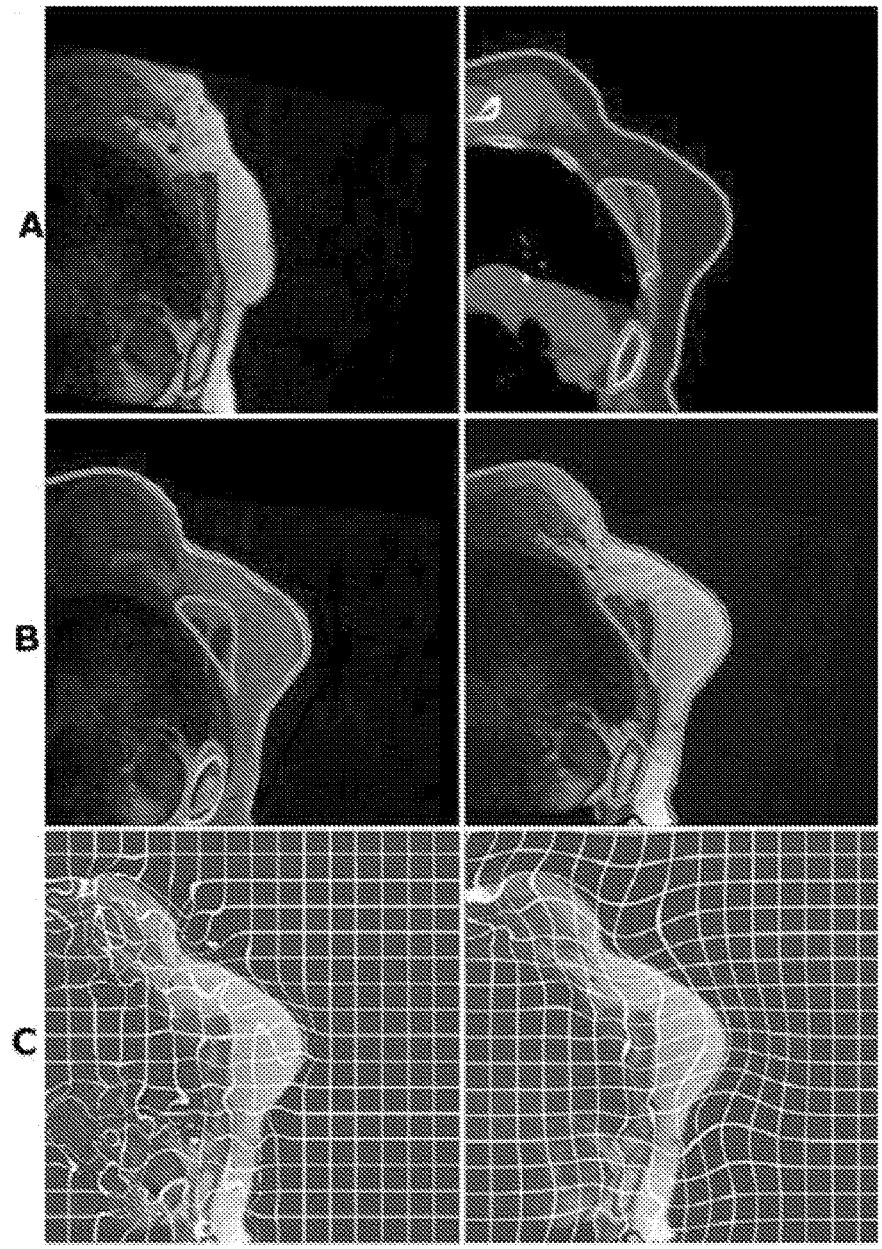
FIG. 10 shows an example of bending energy limited diffeomorphism (BELD)-regularized deformable image registration (DIR) for a breast cancer case with the patient in supine position, in accordance with the present disclosure.

This approach, was tested in a variety of clinical cases. FIG. 10 shows an example of BELD-regularized deformable image registration applied to a breast cancer case, with the patient in supine position. From left to right, images in panel (A) show the original MR and CT images, respectively, where the CT image contains contours structures. Then, the image on the left of panel (B) shows contours transferred from the CT using a DIR with conventional un-regularized method, along with the respective transformation field on the left of panel (C). By contrast, images on the right panels of (B) and (C) show the transferred contours and deformation fields, respectively, using the BELD regularized approach, as described. FIG. 10 demonstrates the improvement of using BELD regularization over the conventional (un-regularized) method for a breast cancer case with patient in the supine position. It is clear that the un-regularized DIR results in an unrealistic deformation field with reduced registration accuracy. By contrast, both deformation field and registration accuracy are improved with the BELD regularization of the present disclosure.

Figure 11:
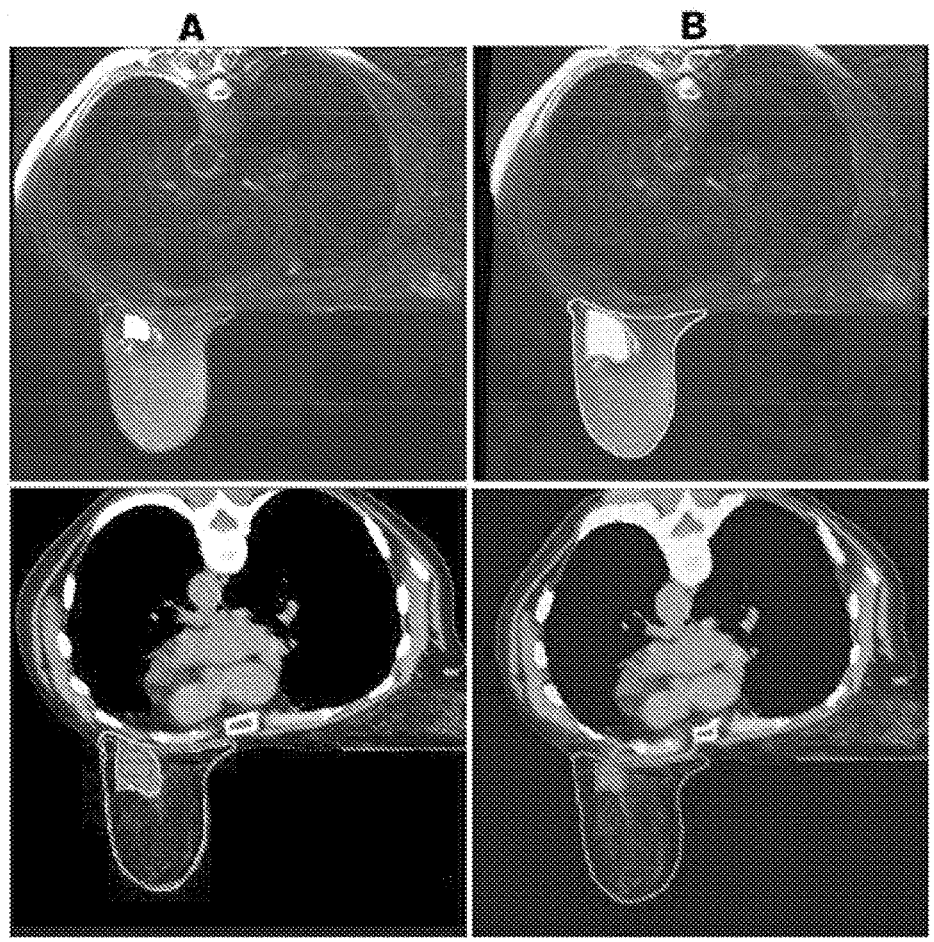
FIG. 11 shows an example of BELD-regularized DIR for a breast cancer case with the patient in prone position, in accordance with the present disclosure.

FIG. 11 shows an example of BELD-regularized DIR for a breast cancer case with a patient in prone position. The top and bottom images show original MR (top) and CT (bottom) images, respectively. Panel (A) shows breast and lumpectomy cavity contours from the MR image overlaid onto the CT (bottom) image using a rigid registration algorithm. By contrast, the top image of panel (B) shows contours transferred from CT to MR, while the bottom image of panel of (B) shows the transferred contours from MR to CT, based on the BELD-regularized DIR. Blue contours are deformed from the red contours on the original MR images. Comparing to un-regularized registration, which resulted in a difference between the actual and transformed contours up to 10 mm (average of 4.2 mm), the BELD-regularized DIR reduced the average difference to 1.8 mm. This demonstrates that the present disclosure allows for contours of breast and lumpectomy cavity to be accurately transformed from MR to CT for using in radiation treatment planning.

In addition, this approach was also tested for CT and MR images of pancreatic cancer patients acquired at the same respiration phase to minimize motion distortion. Dice's coefficient was calculated against direct delineation on a target image. Contours were generated by various methods, including rigid transfer, auto-segmentation, deformable only transfer and regularized b-spline method, as described above, were compared. Although fuzzy connected image segmentation involved careful parameter initialization and user involvement, automatic contour transfer by multi-modality deformable registration, as described, provided up to 10% of accuracy improvement over the rigid transfer. Providing two additional steps of adjusting intensity distribution and modifying the deformed contour with affinity map may further advantageous improvement up to 14% in transfer accuracy.

Figure 12:
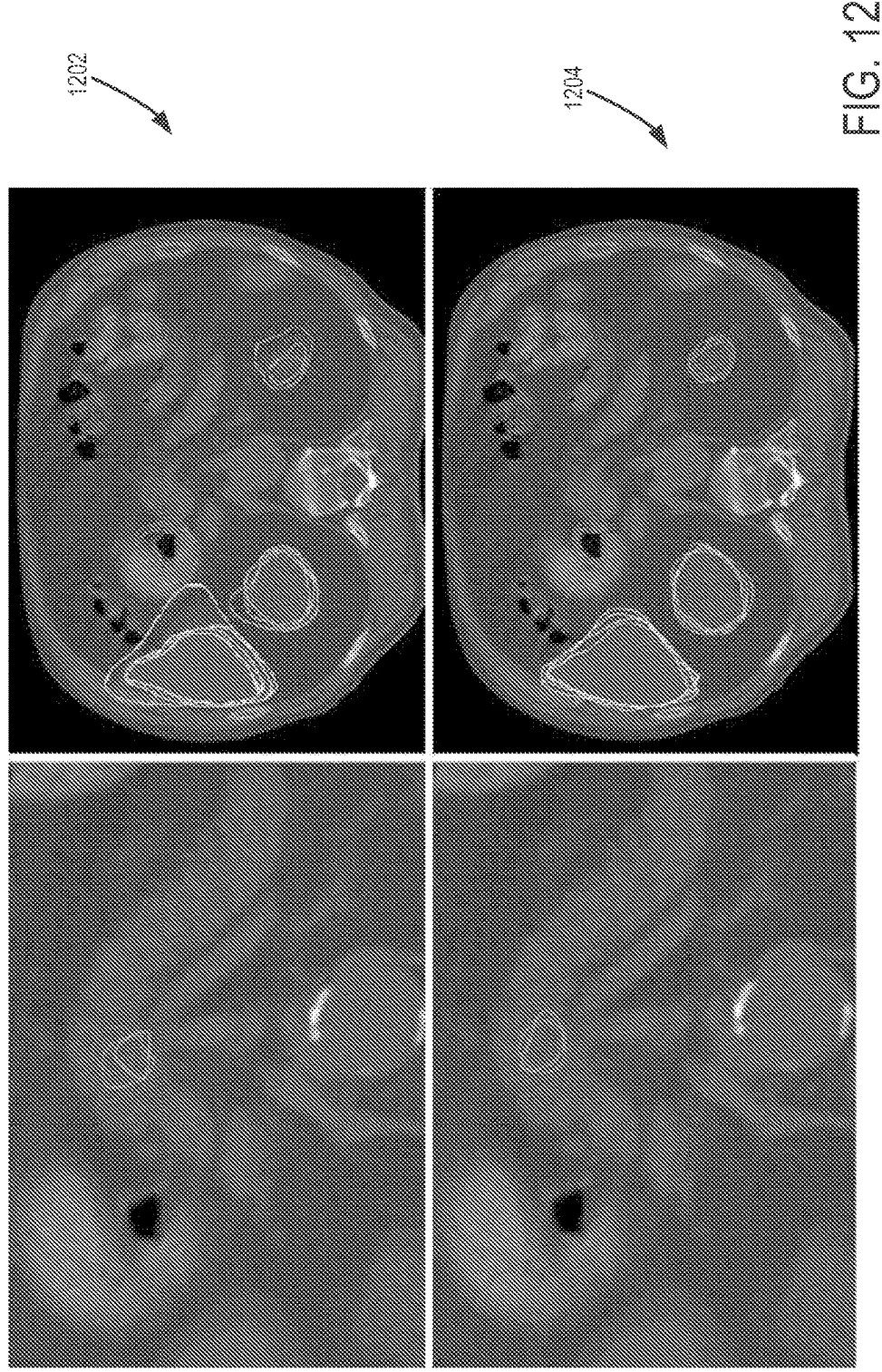
FIG. 12 shows example images illustrating multi-modality contoured structures resulting from application of deformation fields, in accordance with the present disclosure.

FIG. 12 shows an example of results from multi-modality contoured structures treated by deformation fields in accordance with the present disclosure. Specifically, PET, and various MRI including T1, T2, DWI and DCE, were rigidly registered with CT images for representative patients with pancreatic cancer. Gross tumor volume (GTV) and organs at risk (OARs) were delineated on the multi-modality images and were processed using a deformable multi-modality image registration tool, as described. Substantial variations among contours from multi-modality images were observed for both GTV and OARs, as illustrated in FIG. 12. The upper two images 1202 of FIG. 12 show a large variation in volume from several structures among the different overlaid contours generated using multi-modality images. Derived deformation fields were then applied to deform the corresponding modality contours, which were subsequently overlapped onto the planning CT. The lower two images 1204 of FIG. 12 show increased overlapping among different modality contours after treated using deformation fields. When using T1 weighted contour volume as nominator, the delineated volumes vary from 0.5 to 1.8 for GTV, from 0.81 to 1.05 for OARs between the image modalities. The overlapping ratio between different modalities varies from 0.22 to 0.74 for GTV, and from 0.65 to 0.84 for OARs. After deformable image registration, the contour volumes were changed by deformation fields by 6% to 11%. The remaining variations after DIR observed in FIG. 12 were mostly due to the inherent difference between the imaging modalities. These changes do not impact volume variation between different modalities, but improve significantly the overlapping ratio between contours from different modalities, for example, changing from 0.55 to 0.82 for GTV. Therefore, deformable image registration of multi-modality images increases the agreement between contours from different image modalities, improving accuracy for target and normal structure delineation for radiation treatment planning of pancreatic cancer.

Registration algorithms often make use of a smoothing kernel to reduce discontinuities in the deformation field applied between iterations. In another aspect of the present disclosure, a novel method is provided for implementation in systems and methods configured to perform image registration, wherein the dimensions of the Gaussian smoothing kernel is adaptively modified during runtime according to a threshold, such as a rate of convergence for the deformable image registration. In particular, a large kernel size may be used initially and then reduced through subsequent iterations. With other approaches, as the iteration number increases, the rate of convergence begins to decrease until an asymptotic value is reached. At this point, the accuracy of the registration remains unaffected by further iterations. By contrast, in the present disclosure, varying the kernel size allows for asymptotic convergence to be avoided and the accuracy may then be able to continue toward a new range of possible values. In this manner, as the size of the smoothing kernel is stepped down, the accuracy continues to improve. This approach has several advantages benefiting improved registration accuracy over traditional methods employing demons-based registration algorithms. Specifically, one advantage is that the kernel is robust enough to handle large deformations, such as those found in the bladder and rectum, yet sensitive enough to handle fine details, and also is typically immune to non-physical warping. Additionally, it also provides for a spatial alignment between common structures in the images, making further registration easier.

Figure 13:
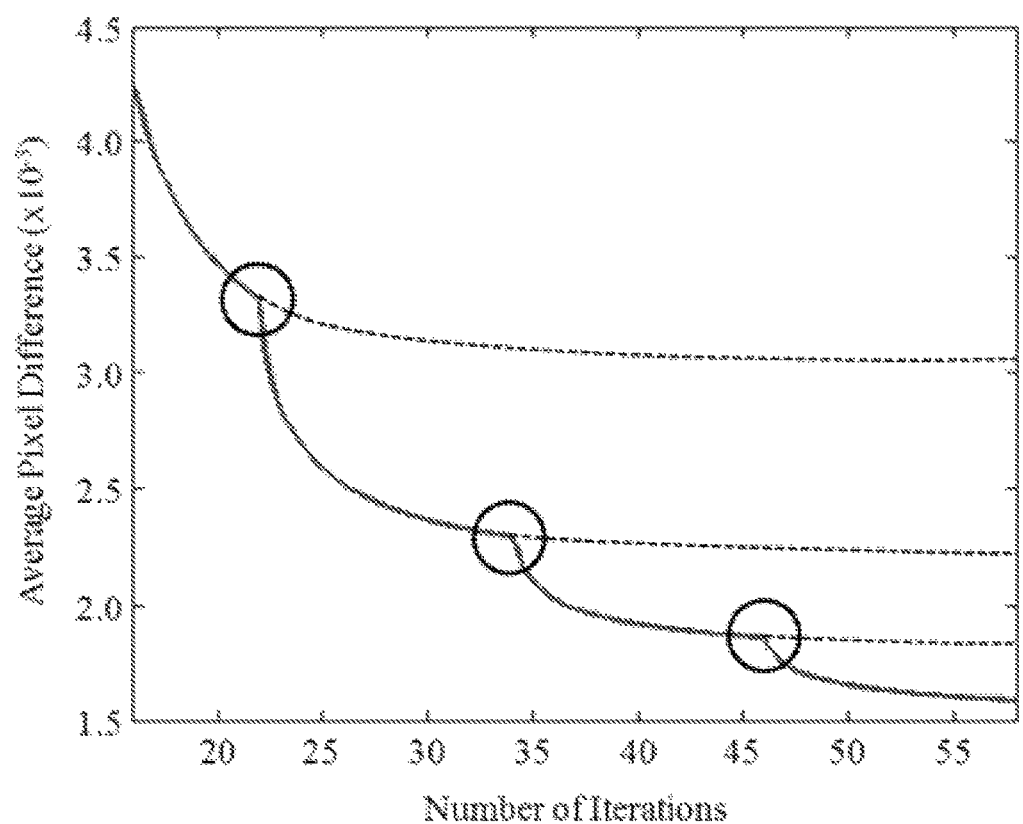
FIG. 13 shows a graphical example demonstrating the effect of a variable-kernel smoothing technique on registration accuracy, in accordance with the present disclosure.

FIG. 13 shows an example demonstrating the effect of a variable-kernel smoothing technique on registration accuracy. Typically, the accuracy improves after a number subsequent iterations, as indicated by a decrease in the average pixel difference between the images. However, when only using a given kernel size, the accuracy begins to converge to a constant value (dashed lines). As such, by adjusting the size of the kernel adaptively (circled regions) when a specified condition is met, pre-mature asymptotic convergence can be avoided, and the algorithm allows for transition to a new range of possible values. This leads to improved registration accuracy, exceeding the limits possible with a constant kernel size.

Such approach allows for fast and accurate deformable image registration of cone beam CT (CBCT) and CT images, typically employed in online adaptive radiotherapy. Tests showed that a variable-kernel method resulted in improved accuracy, beyond that for a constant kernel size. Specifically, the planning CT and daily CBCT acquired for 6 prostate cancer patients were registered using the above-described technique. Histogram matching was used to compensate for intensity differences between the two modalities. The Pearson correlation coefficient (PCC) and volume overlap index (VOI) were used to quantify registration accuracy. Results showed that the iterative decrease of the smoothing kernel size allowed the algorithm to converge to an increasingly accurate solution, beyond the asymptotic limit for a constant kernel size. The mean VOI was calculated for bladder, prostate, and rectum with values of 91.9%, 68.7%, and 78.2%, respectively. The correlation coefficient was calculated for every fraction in the overlapping CT and CBCT scan volumes in each patient data set. Average PCC values were 0.9987, 0.9985, 0.9982, 0.9980, 0.9985, and 0.9985 for the six patients. A typical runtime for a 512×512×70 image volume was 4.6 minutes. Therefore, results using DIR technique of the present disclosure validates its use for deformable CT-CBCT registration, eliminating the need for multi-resolution processing and continual up-sampling of the image, which can be computationally intensive.

Figure 14:
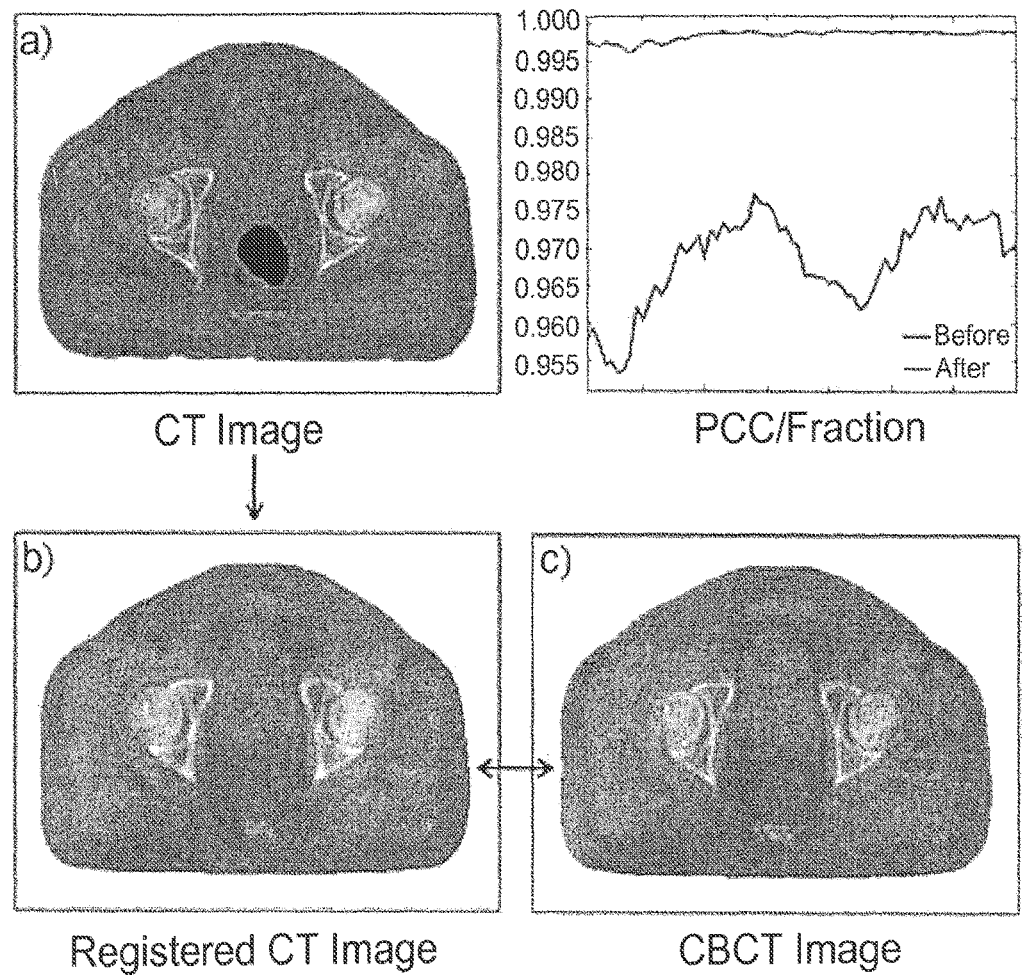
FIG. 14 shows image results from a registration using a variable-kernel soothing applied to pelvic CT scans, in accordance with the present disclosure.

To illustrate the robustness of the described algorithm in processing large deformations, as seen, for example, in typical prostate cancer cases, FIG. 14 shows registration results for a pelvic CT scan. Specifically, a planning CT (a) was deformably registered to a daily kV cone beam CT (c) using the described technique. The resulting image (b) was in excellent agreement with the CBCT image. The included plot displays correlation coefficients for the entire image volume (70 slices) before and after registration, demonstrating the consistency of the method. This demonstrates the technique's ability to process relatively large deformations, with particular with reference to the rectal area, where the algorithm was able to compensate for considerable warping of the surrounding tissue. Noticeable differences exist between the preregistered images, after registration, the resulting images agree very well.

Additionally, intra-modality DIR techniques make use of the Demons algorithm to provide intensity mapping for the conversion of several modalities to CT-like contrast scales. These may operate on varying types of CT (e.g., cone beam CT, MVCT), as well as ultrasound (US) images. In particular for US, such approaches may implement a correspondence function designed specifically for ultrasound. However, a simple relationship between tissue echogenicity and CT Hounsfield units has yet to be established. As such, current US-CT registration practices have been limited to rigid registration or the use of inter-modality methods, such as thin plate splines, which require manual point selection.

High-frequency ultrasound (HFUS) images are capable of revealing accurate spatial information, for example, in skin lesions, and may be used to plan and guide radiation therapy (RT) for skin cancer. Therefore, in yet another aspect of the present disclosure, systems and methods are provided for performing fully-automated, accurate deformable registration between US and CT images, which may be beneficial for skin cancer patients requiring radiotherapy treatments. Specifically, a novel DIR technique is introduced, based on the symmetric force Demons algorithm, in which the size of the Gaussian smoothing kernel may be adaptively adjusted. A correspondence function may also be used to map attenuation values to tumor elasticity and a histogram matching may implemented. The Pearson correlation coefficient (PCC) may be used as an indicator for assessing registration accuracy.

This approach provides robustness to the algorithm, as described, under the large deformations, typically encountered during skin tumor shrinkage. Since skin lesions, in particular, have the added benefit of a clear external boundary, the present disclosure also facilitates use of an anisotropic diffusion filter to perform edge-preserving smoothing, thereby reducing noise and increasing registration accuracy. Such advantages may be particularly important for superficial US images, which can suffer from poor image quality and low contrast. Additionally, the intensity matching technique typically used to convert between different CT image types, may also be applied to US images acquired at different frequencies, making US-US registration possible.

Figure 15:
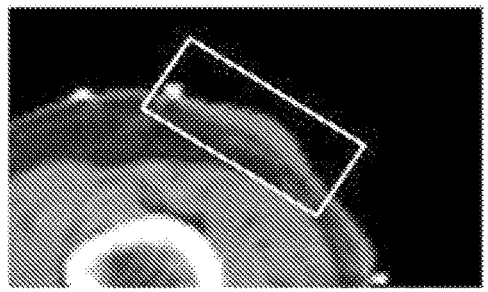
FIG. 15 shows an example illustrating a registration between CT and high frequency ultrasound (HFUS) images for a patient with a superficial basal cell carcinoma.
Figure 15:
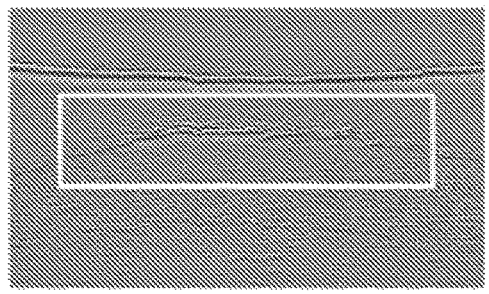
Figure 15:
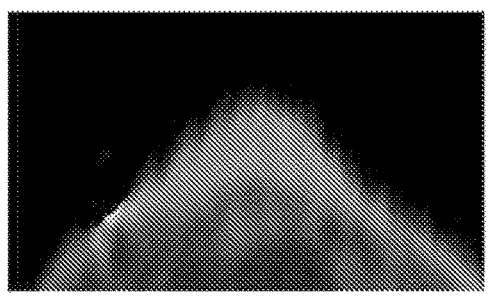
Figure 15:
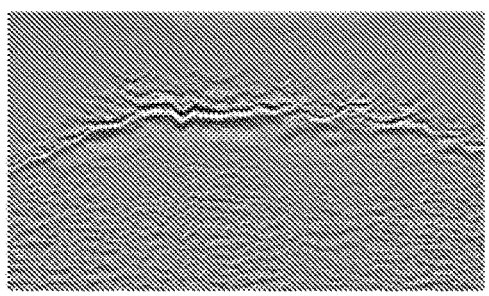
Figure 15:
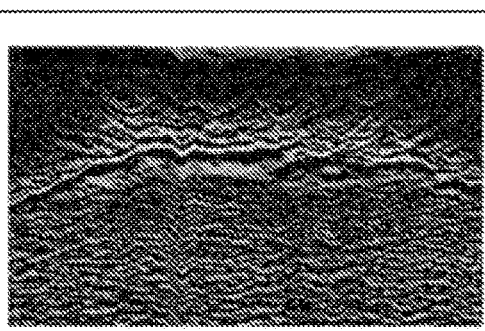
Figure 15:
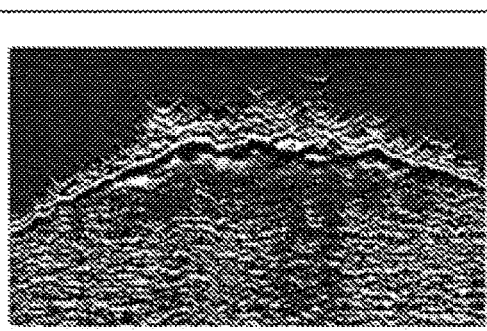
Figure 15:
Figure 15:
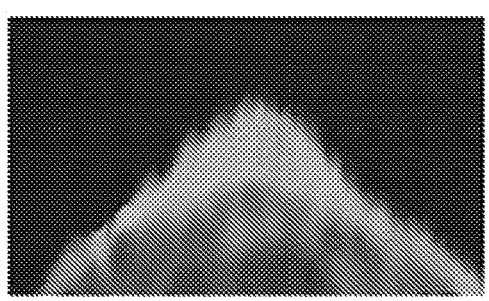

To demonstrate the feasibility of this approach, HFUS images of skin lesions and their corresponding CT images were registered for selected regions of interest (ROI), in accordance with the present disclosure. FIG. 15 shows an example illustrating a registration between CT and HFUS for a patient with a superficial basal cell carcinoma (BCC) in the thigh. The figure shows the CT (a) and high frequency ultrasound (b) image of the lesion, while c) and d) are enlarged views of the rectangular regions in a) and b). e) and f) are the histogram-mapped and the contrasted-enhanced HFUS images, respectively, and g) and h) are registered images of CT and HFUS using the above-described variable kernel smoothing technique. PCC values of 0.9794 and 0.9815 (enhanced contrast) were observed, indicating excellent agreement between the dynamic (HFUS) and static (CT) images. The registration technique also exhibited an ability to process large deformations, such as ROI displacement exceeding 200% of tumor thickness observed near lesion edges. The gradual decrease of kernel dimension was found to prevent non-physical warping, thereby improving registration accuracy. This robustness is critical to skin cancer RT as tumors may shrink significantly during treatment.

Therefore, combined with standard image processing techniques, the method of the present disclosure is sufficiently accurate to achieve deformable registration of HFUS and CT images for skin cancer RT. This may be advantageous in the ability to perform image-guided treatment for skin cancer, which could reduce geographic missing and may spare more healthy tissue. The presented technique is accurate and robust enough to process large deformations, making it a promising tool for RT planning and delivery guidance for skin cancer.

Software tools for use in multiple-modality image registration, as described, may achieve physically accurate registration with minimized user interference and computation cost, making multi-modality deformable imaging registration fast and accurate, in particular within the context of ART re-planning or other real-time applications. Specifically, the approach of the present disclosure may improve the accuracy of contour transfer between different image modalities under challenging conditions of low image contrast and large image deformation, in contrast to common methods utilized in radiation treatment planning.

Returning to FIG. 1, at process block 14 processed multi-modality images, as described, may then be received, for example, from an imaging system or a data storage, and transferred to a planning system for use in generating a radiotherapy plan. Specifically, in the case that a plan is formulated for a first treatment, this process step typically includes the determination of beam or radiation source delivery techniques and arrangements based upon selected or determined planning aims. In certain planning approaches, this may include generating beam's eye-view displays, designing field shapes (blocks, multi-leaf collimators), determining beam modifiers (compensators, wedges) and determining beam or source weightings. Using contoured critical structures, performed either manually or using an automatic contouring tool, dose calculations may then performed based on selected algorithms or methodologies. Using set relative and absolute dose normalizations and dose prescriptions, a plan quality is then evaluated based on visual coverage comparisons, dose volume histogram analysis, and tumor control and normal tissue complication probabilities. Automated or semi-automated optimization tools may then allow for plan improvement based on the planning aims and tolerances.

In some cases, generated plans may also involve taking into account intra-fractional motion, such as respiration motion, of target and critical structures. Thus, in accordance with some aspects of the disclosure, a 4D planning approach for intra-fractional motion based on 4DCT or 4D MR images partitioned into, for instance, 5 phases, although other values are possible, includes the following aspects: (i) creating an IMRT or VMAT plan for one specific breathing phase (e.g., end of inhale) based on the phase image by a full scale optimization, (ii) populating this plan onto the other remaining breathing phases by applying segment aperture morphing (SAM) algorithm to take into account changes of the anatomy between breathing phases, and (iii) combining all phase-specific plans to form a 4D plan. Essentially, all phase plans have the same number of segments, with each segment having several different MLC patterns, dependent upon the number of phases, with the same MU, jaw settings, gantry angle, etc. The 4D plan generated in this way may be delivered using dynamic MLC and adjustable dose rate such that each segment can be delivered within an integer number of breathing cycles, ensuring that each MLC pattern is delivered with its corresponding breathing phase. In particular, the delivery file from the multi-leaf sequencer is generated as a function of breathing period. At each treatment fraction, the delivery file can be quickly updated with the breathing period obtained immediately prior to the delivery. If breathing cycle changes during the delivery, the delivery file can also be updated with the necessary frequency during the delivery.

For situations when respiration is substantially different as compared to when the planning images was acquired, an online adaptive 4D planning and delivery may be implemented in the following steps: (1) a reference plan is generated based on a single-phase image (reference phase, e.g., end of inhalation) from the planning image sets; (2) a comprehensive dry-run QA will be performed for the reference plan; (3) at the time of a treatment fraction, the reference plan is modified using the SAM algorithms based on the anatomy change on the reference phase image of the 4D images acquired with patient in the treatment position immediately prior to the treatment delivery; (4) the newly created reference plan (adaptive plan) is populated based on each of the remaining phase images of the day using the SAM algorithms; (5) all phase plans are then sequenced taking into consideration the most current breathing information; and (6) the 4D plan is delivered under real-time image guidance (e.g., orthogonal cine MRI) and its delivery may be interrupted if MLC fails to track the target due to the abrupt changes in patient positioning or respiration motion.

Changes to targets and critical structures between treatment fractions, or over the course of several fractions, may produce significant deviations from the original plan, with potentially negative impacts in treatment efficiency. As such, providing a radiotherapy plan at process block 14 may, in some cases, involve performing applying techniques for adaptation of an original or first plan, such as those afforded by ART, to account for patient-specific anatomic and/or biological changes during the course of treatment, using any combination of online and offline approaches, as will be described.

Traditional plan optimization approaches are not typically fully automated, since often the optimization algorithm delivers undesirable results, requiring additional iterations with different weighted objectives. This is due to the difficulty in estimating how much can be achieved for different planning objectives, commonly defined in terms of dose-volume constraints. For instance, some objectives may be formulated as portion of an organ or structure not being allowed to exceed a dose. As an example, one such objective can be that 30% of a rectal volume cannot receive a radiation dose of more than 60 Gy.

If an individual OAR's objective is too stringent, as when a dose-volume is placed too low, or a relative weight of the goal is too high compared to other objectives, this may create undesirable effects, such as insufficient tumor coverage or radiation dose hotspots. Since volumes of OARs change as often as day-to-day, it may not possible to know exactly how much OAR radiation sparing is possible, or specifically what minimum percentage of volume needs to be irradiated for certain amounts of doses. Therefore, the iterative process of finding the right objective weighting is tedious and time-consuming, requiring expertise and experience.

Previously proposed technologies aiming to overcome this obstacle attempted either to determine the best achievable dose volume histogram (DVH) by computing OAR/target overlapping fractions or utilized multi-parameter criteria optimization, where each objective is separately optimized and a linear interpolation is then performed to determine an appropriate compromise. In particular, the multi-criteria optimization method is impractical for online ART since it requires several optimizations. In addition, both methods are designed for initial plan optimization, not re-planning, and require whole set of OARs to be generated.

Contours obtained by organ delineation are a time consuming part of any online adaptive re-planning, with OARs typically representing the majority contours to be delineated. Specifically, organs around the digestive tract, such as liver, rectum, bowels, and stomach are very problematic, since they are large organs and require many contours. In addition, their size, shape and content changes drastically and unpredictably from day to day, which makes it very hard for the auto-contouring methods to accurately generate contours, typically requiring human delineation/editing.

As described, fast online re-planning methods require efficient approaches to modifying radiotherapy plans, often while a patient lies on the treatment table. To overcome the drawbacks of previous online re-planning methods, in another aspect of the present disclosure, systems and methods are provided that make use of a novel Gradient-Maintenance (GM) algorithm that allows for fully automated online ART re-planning without the need of OAR contouring.

As will be described, the GM algorithm calls for creating or adjusting beam or segment apertures based on a target of the day, and optimizing beam or segment weights using either ring structures generated autonomously or semi-autonomously or isodose contours automatically converted from isodose lines on, for example, an image of the day. The algorithm determines dose gradients from the dose distributions in the original plan for each of the critical structures in the vicinity of the target, and initiates a re-planning optimization procedure aiming to maintain the originally planned dose gradients. The algorithm can enhance automation, drastically reduce planning time, and improve consistency throughput of online re-planning.

Specifically, unlike methods that try to determine, in a time-consuming fashion, "what is achievable" such that optimization goals may be set, the approach of the present disclosure efficiently determines dose gradients, providing a direct measure of "what can be achieved," imposed by physical dose deposition limitations. In this manner, transfer of dose gradients from the original to the modified plan may result in the best plan achievable with respect to allowed physical dose deposition constraints. Such approach affords several advantages over previous technologies. Specifically, generation of organs at risk (OAR), for example, on a daily basis may not required, thus reducing delineation practice to only the treatment target. In addition, traditional optimization algorithms strive to satisfy a group of objectives, specified in terms of dose volume constraints for each of the OAR, which usually requires volumes to be generated, for example, on daily image sets. By contrast, the approach of the present disclosure strive to arrive at certain dose gradients from the surface of the target toward each organ at risk, allowing the optimization to be more reproducible and predictable, and less likely to require multiple trial and error iterations. In this manner, human involvement may be reduced or eliminated along with and time cost of optimization, which is an attractive feature for fast online re-planning.

Figure 23:
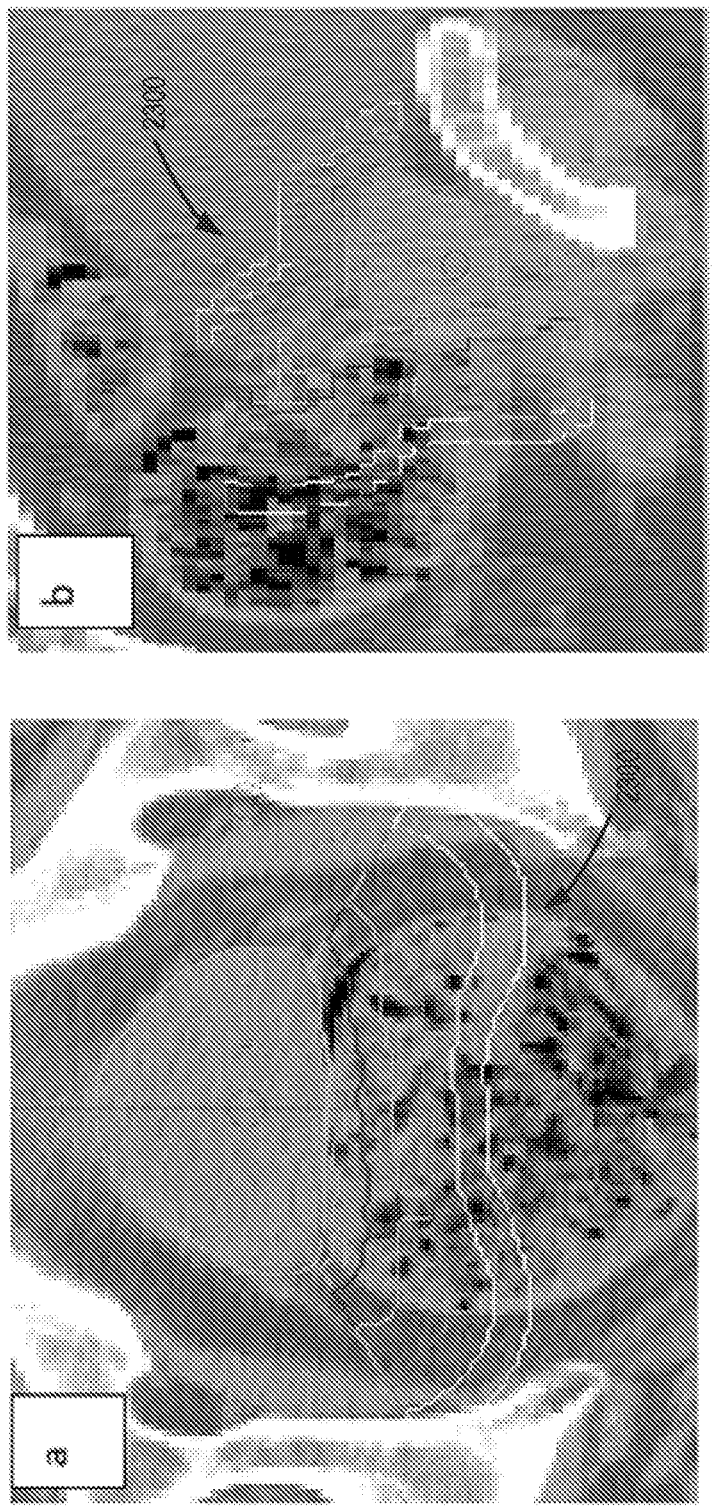
FIG. 23 shows examples of partially concentric rings utilized in a fast online re-planning approach, in accordance with aspects of the present disclosure.

The GM algorithm, as described, may be configured to work within dedicated optimization software and hardware, or may be combined along with systems configured for fixed- or rotational-beam radiation delivery, or combinations thereof. In some envisioned implementations, maintaining dose gradients from the surface of the target, as described, may be achieved by having a planner communicate desired planning goals to an optimization algorithm via a weighted sum of goals called "objective function," which, in some aspects, may be generated using the dose gradients. Since many commercially available optimization systems only permit objective functions to be defined in volumes of interest and dose-volume goals, the approach of the present disclosure may be adapted to allow for user-generated partial concentric ring structures (PCR) to be employed in defining the desired dose gradients for the optimization algorithm. As such, any desirable system or methods may be used to generate PCR. For example, PCRs may be generated using manual or auto-contouring approaches. Anatomical sites that would benefit most from the approach of the present disclosure could be prostate and pancreas, given the large number of surrounding OAR structures, with typically large daily unpredictable volume changes and relatively small target organ sizes. Example PCRs 2300 are illustrated in FIG. 23 for a prostate cancer case.

Figure 16:
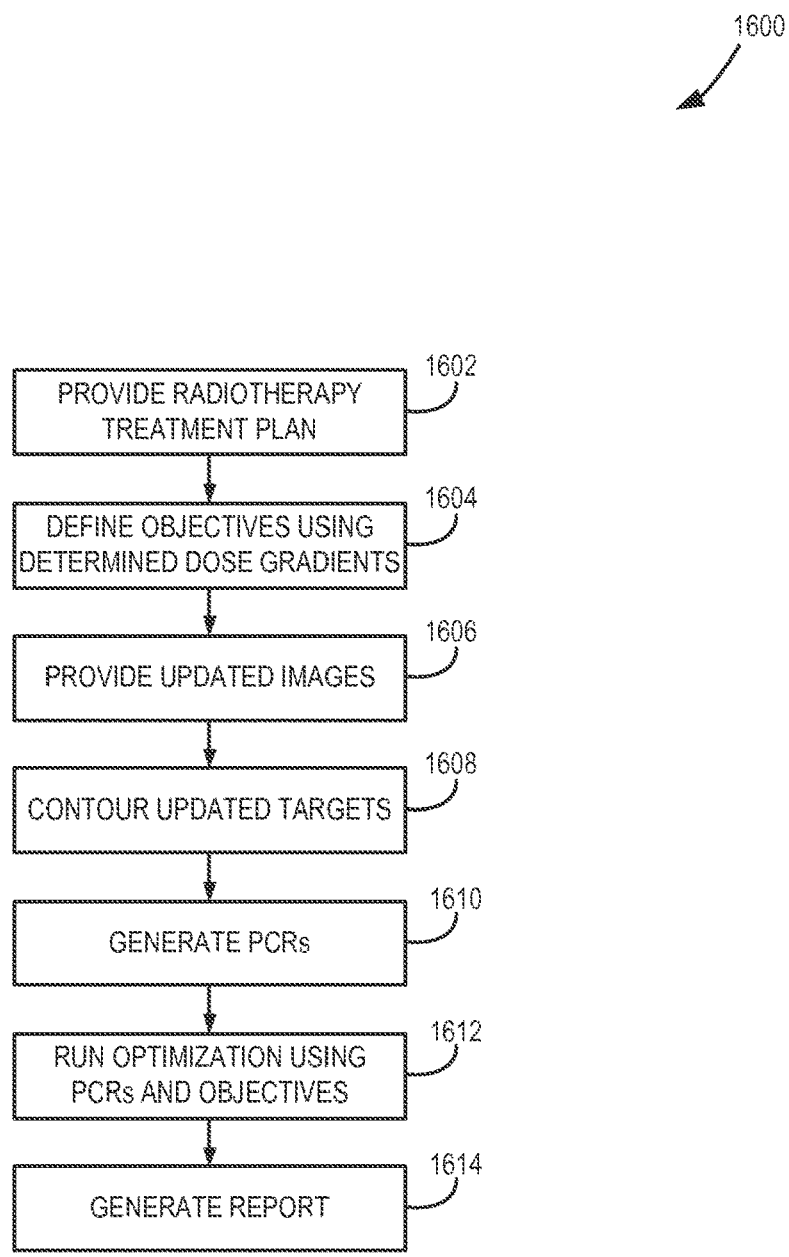
FIG. 16 is a flowchart setting forth steps associated with a mode of operation for a gradient-maintenance algorithm, in accordance with the present disclosure.

Turning to FIG. 16, an example online plan adaptation process 1600 is shown, illustrating a mode of operation for the GM algorithm. In particular, such process 1600 may be utilized when any condition has been met that would trigger a plan modification, such as, for example in the case of reduced target coverage or increased radiation dose hotspots. The process 1600 begins at process block 1602, where a radiotherapy treatment plan is provided as input to any systems configured to carry out the process 1600, such as a treatment planning or delivery station. The treatment plan input, defined at least by a radiation dose distribution, may be a plan generated at the onset of treatment schedule, or may be a subsequently modified plan. In some aspects, a plan may be generated at process block 1602 using conventional planning techniques, such as IMRT optimization. Such plan can achieve the desired dose-volume objectives for both targets and OARs using full sets of contours on planning images, and can be a best possible plan for the planning technique utilized, given that the planner is not necessarily under a time constraint.

At process block 1604, using the radiation dose distribution from the provided or generated plan, dose gradients are determined defining a variation in radiation dose from at least one target structure toward any or all of the non-target structures or objects at risk. Such dose gradients may be used in defining any number of optimization objectives, which may be desirable in an online plan optimization process, as described. In particular, radiation dose distributions in treatment plans already subjected to an optimization may potentially represent an optimally achievable solution for desired dose constraints, and thus may prove to be good starting point in an optimization process.

Then, at process block 1606, updated image information is provided, which may include a multi-modality image set. For example, the updated image set may include any number of magnetic resonance images, computed tomography images, ultrasound images, positron emission tomography images, and synthetic electron density images, or any combinations thereof. The updated image information may then be used at process block 1608 to generate contours of any updated target volumes. As described, such contours may be generated autonomously or semi-autonomously.

The updated target contours may then be used, at process block 1610, to generate PCR structures arranged generally in relation to, or about the updated contours of targeted structures. In some aspects, the PCR structures may be centered about the updated target contours and directed towards any or all non-targets, or objects at risk, and points along a dose volume histogram of the PCR structures may be used to generate an objective function for use in the optimization process. Then, at process block 1612 an optimization process may be performed using generated PCR structures along with objectives defined in accordance with determined dose gradients from process block 1604. During the optimization process, which may require any number of iterations, the objective function may be modified according to defined objectives, to achieve targeted dose constraints or dose gradients, for example, dose gradient from surfaces of the updated target volumes in relation to any or all non-target or objects at risk.

Then, at process block 1614, a report is generated, representative of the adapted radiotherapy plan obtained from the plan optimization process, which may take any shape or form, as desired or required by a treatment plan verification or delivery system.

Since, as described, contoured structures may be subject to deformable registration using standard algorithms, which typically do not provide very accurate and reliable contours, direct usage of deformed contours may prove problematic for some daily plan optimization schemes. By contrast, the GM algorithm may not require contours to be very accurate since only the relative positions of the structures may utilized, and variations in the organ shapes may not affect the accuracy of the PCR. For example, to generate a PCR toward a certain critical structure, one may only need to know what part of the ring surrounding the target will be toward that critical structure. Therefore, the PCR area is the projection of that critical structure to the surface of the target or the ring. Since the 3D volume information of the critical structure is collapsed (projected) onto the 2D target surface to determine the portion of the ring that is toward that critical structure, the inaccuracies in the volume of the critical structure are largely diminished by the collapsing. Moreover, margins may be applied around the ring areas, for example, a margin of 3 mm. For very large structures such as bowels, only part of the critical structure that is within a certain distance (e.g. 2 cm) of the target may be included. Additionally, it is possible to generate the PCR for certain organs in an easier way, for example the rectum, where one can have the PCR cover the whole range of posterior directions from prostate surface.

For some structures, such as a bladder, auto-contouring can achieve daily contours with adequate accuracy. As such, use of PCRs may provide similar time reduction in terms of contour delineation. However, since a bladder volume changes drastically from day to day, this would make the optimum objective weights in the objective function difficult to predict. Therefore, a PCR-based optimization may still advantageous in the sense of providing for a more predictable optimization, as mentioned above.

In a study, the approach of the present disclosure was investigated to quickly generate adaptive plans. Using daily treatment CTs, only target structures (CTVs) were delineated. Then PCR structures of uniform thickness, namely 3 mm, were automatically generated using an in-house program. There were separate PCR structures toward each of the important critical structures surrounding the target. This was accomplished by first generating rings surrounding each target all around, and then finding the intersection of the rings with the projection of each OAR. Several ring structures for each OAR were formed, such as PCR#1: from 0 to 3 mm, PCR#2: from 3 to 6 mm, PCR#3: from 6 to 9 mm, and so on.

Figure 17:
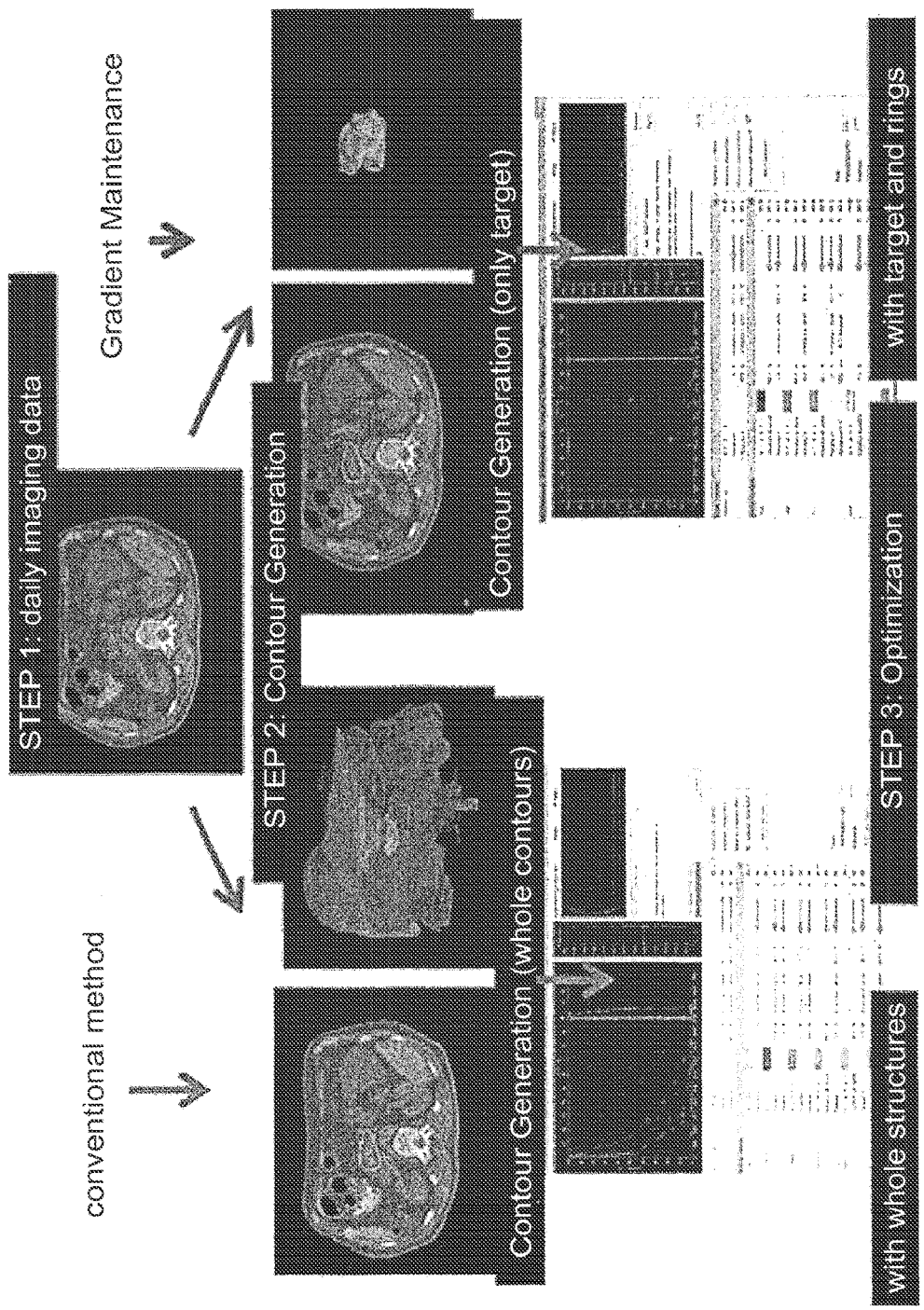
FIG. 17 shows a diagram comparing online re-planning schemes using a conventional and gradient-maintenance approach, in accordance with the present disclosure.

FIG. 17 shows a diagram illustrating an example comparing online re-planning schemes using conventional (left) and GM (right) method in three steps, namely daily image acquisition, contour generation based on daily images, and plan re-optimization based on new contours. In the conventional method, the full set of contours are needed in Step 2 and the original objective functions, which can be a complicated set of dose-volume constraints, are used in the subsequent plan optimization. By contrast, the GM method of the present disclosure provides for a simplified approach with significant planning time savings, whereby only the target and PCR contours, which may be generated automatically, are needed along with determined dose gradients.

Given that initial planning is typically not under the time constraints of online planning, an original plan may be generated in any fashion, for example, using the original volumes and dose-volume constraints. Such original plan may describe the best plan achievable, which would possess the steepest dose gradients achievable toward each OAR. Using an original plan with a nominally optimum dose distribution, several points along the DVH of generated PCRs were recorded and used to generate an objective function which as stored for online re-optimization. The optimization step was then performed using the newly generated PCRs along with the stored objective function. To quickly reach dose gradient goals, the optimization of the adaptive plan started from the original plan on the image of the day. Since the dose gradients may be the best achievable, each of the objective goals (for each PCR) was set to the exact DVH points obtained from the original plan, and weighted equally.

This approach, as described, is different from common optimization practice, where the DVH objectives are almost always set to points that are "better than actually desired," making the optimization process unstable and prone to undesirable results. Since, in the approach of the present disclosure, it is known what can be achieved from original planning, the DVH goals can be set to those points. The main advantage of this approach is that it eliminates the necessity to delineate the full set of structures, and only requires the delineation of the target, therefore drastically reduces the re-planning time. Also this approach makes daily re-planning more reproducible, eliminating the necessity for trial-and-error effort, since gradients toward each structure are oftentimes achievable (already achieved in an original plan), therefore adjusting the optimization criteria is not necessary for the daily anatomy. On the other hand, standard optimization methods rely on dose-volume-based criteria, which may vary drastically from day to day, due to the variation in the volume of the organs.

It is worth taking into consideration the situation when the volume of the OAR is very small one day and the original dose gradient maintained would lead to unacceptable volume of the organ to receive high doses. Since there are physical limitations to the magnitude of dose gradients, once reached, one cannot increase the gradient any further unless willing to sacrifice other plan quality parameters, such as target coverage. If the steepness of the gradient for one day can be increased without sacrificing the target coverage, this indicates that the dose gradients in the original plan may not have been as high as possible. Therefore it is beneficial that the original plan quality be indeed optimum in terms of dose gradients toward critical structures. If so, the dose gradient cannot be increased any further without sacrificing other parameters, and maintaining the original gradient would satisfy the goal of online re-planning.

Figure 18:
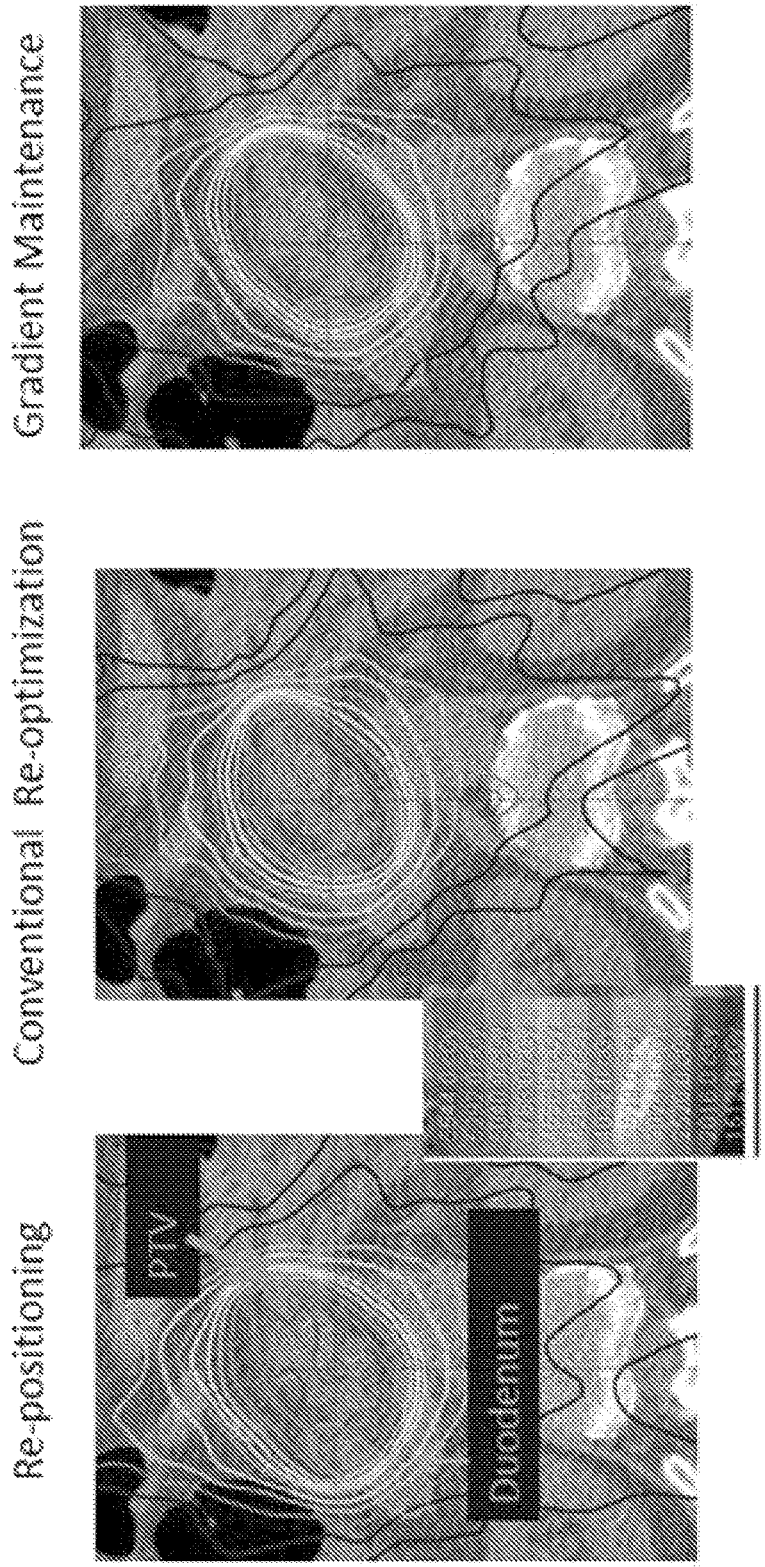
FIG. 18 shows example dose distributions from an image guided radiotherapy (IGRT) repositioning, a conventional full-blown optimization based on a full contour set, and a gradient-maintenance, in accordance with the present disclosure.

FIG. 18 shows an example comparing dose distributions from an image guided radiotherapy (IGRT) repositioning, a conventional full-blown optimization based on a full contour set, and a gradient-maintenance re-planning, in accordance with the present disclosure. It is clear the GM-based dose distribution, for example dose to duodenum, is equivalent to that from the conventional re-optimization, but is substantially improved from that obtained using repositioning. Furthermore, the planning time required for the GM method is only 10% of that required for the conventional re-optimization.

Figure 19:
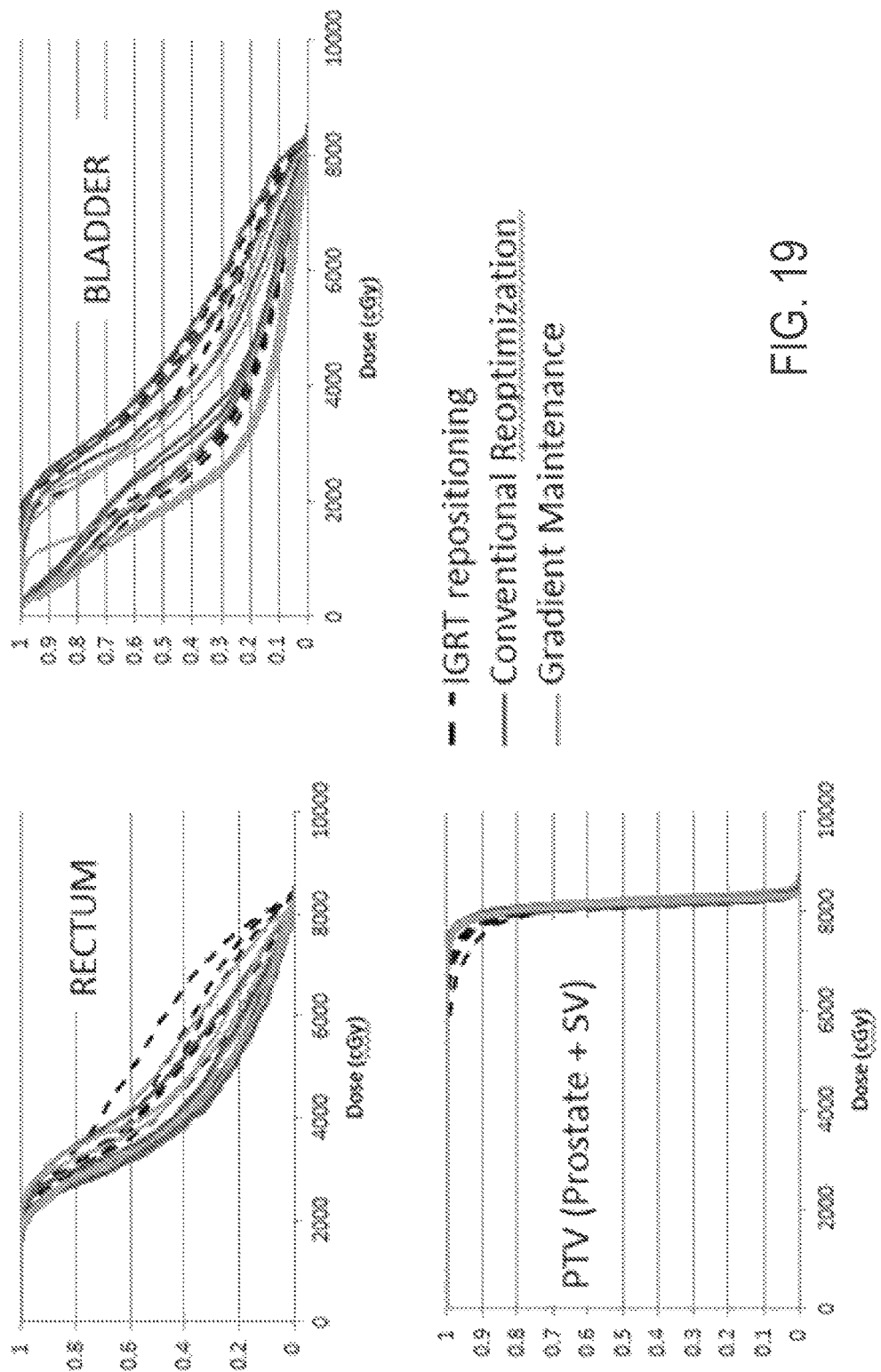
FIG. 19 shows example dose volume histograms for the three strategies of FIG. 18 used to address inter-fractional variations in daily treatments for a prostate cancer case.

FIG. 19 shows an example comparing dose volume histograms for the three strategies of FIG. 18 used to address inter-fractional variations in 6 daily treatments for a prostate cancer case. Once again, it is clear, from the 6 sets of DVHs of the rectum, bladder and planning target volume (PTV) (prostate and seminal vesicle) shown, that the GM-based online re-planning scheme is equivalent to the conventional full-blown re-optimization, and significantly better than the IGRT repositioning method.

Returning to FIG. 1, at process block 16, a number of quality control protocols and procedures for the provided radiotherapy plan may be performed before treatment. As known in the art, such protocols are usually according to treatment systems employed and established clinical workflows, providing verification for the accuracy of the delivery as dictated by the treatment plan. Ahead of radiation delivery, a patient may typically undergo a positional set up and immobilization, and therapists perform a number of positional verifications and adjustments based on pre-treatment imaging, as necessary. Corrections to patient treatment parameters performed while the patients is on the treatment table, classified as "online" corrections, may involve translational or rotational adjustments, as well as modification of the treatment plan using ART, as described.

Then at process block 18, the radiotherapy treatment is delivered, followed by a step of assessing and/or modifying the treatment, at process block 20, to include a report provided by a record and verify system. This step may trigger a number of corrective actions made after the daily treatment has been delivered affecting the treatments of subsequent days. Therefore, in yet another embodiment of the present disclosure, systems and methods directed to implementing an offline optimization process are provided. The offline optimization process consists of computing an accumulated dose delivered using a set of deformably-registered images from previous fractions, for example daily images (CT, MRI or US), and generating an optimized plan for subsequent treatments to correct for any accumulated residual errors from any number of intra-fractional changes, as well other changes not corrected by any online re-planning schemes. For example, residual errors may occur during radiation treatment of prostate cancer, since the prostate may drift systematically or move abruptly due to gas passing through the rectum. Such changes may not be accounted for by an online re-planning using images acquired immediately before treatment.

Figure 20:
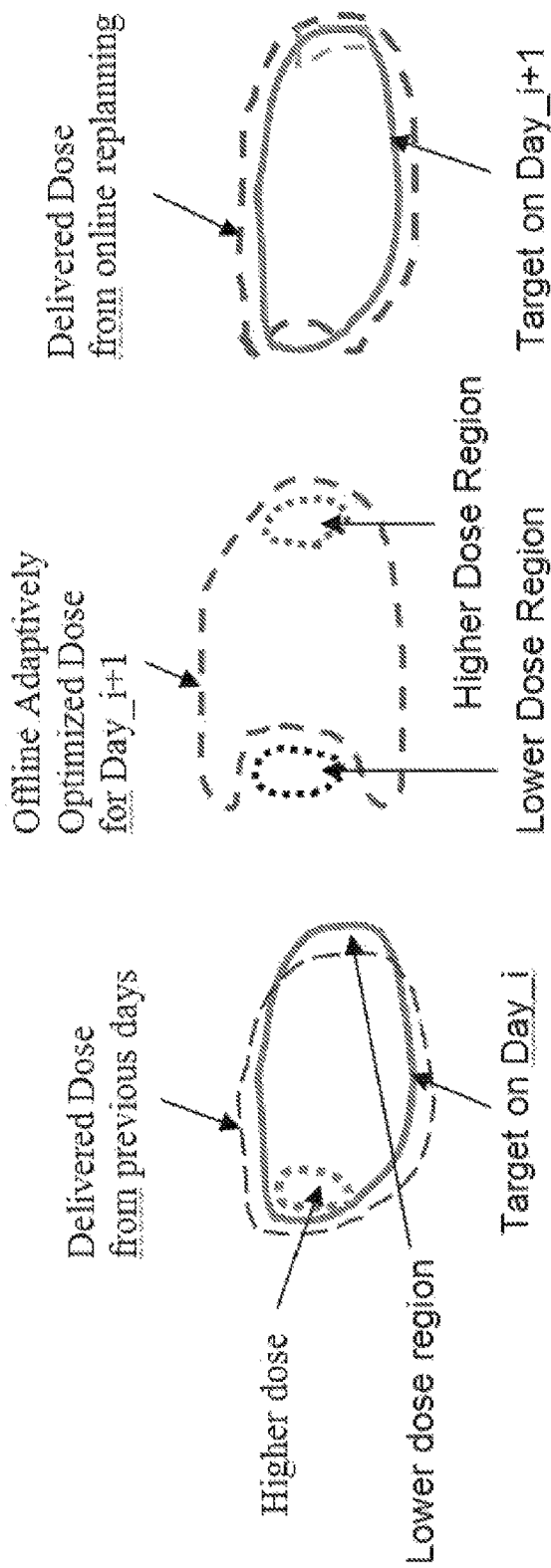
FIG. 20 illustrates an offline optimization, in accordance with the present disclosure.

Specifically, the dose delivered at the any $i^{th}$ fraction using an online re-planning scheme, as described, may be reconstructed by using delivered parameters, for example apertures and monitor units (MU) numbers. The accumulated dose up to that $i^{th}$ fraction may be calculated based on an image of the day using any deformable image registration method. Since both the accumulated dose distribution and the desired dose distribution (for example a gold standard) may be typically generated based on the same image, namely a CT or MRI of the day, the residual errors from intra-fractional changes up to $i^{th}$ fraction not accounted for by previous the online re-planning schemes may be calculated by simply subtracting the accumulated dose distribution from the desired dose distribution. Such residual errors may be provided as input into a planning system to be treated as an initial background, the generated background including both positive and negative numbers. An adaptive optimization with this background may yield an initial plan for use in an online re-planning at a subsequent fraction. For example, FIG. 20 illustrates an offline optimization, as described, potentially to be used in conjunction with an online re-planning method.

The approach of the present disclosure, as described, may be used to correct residual errors after an online re-planning of one or multiple fractions. For a subset of patients, it is likely that an online re-planning, as described, may leave very little error as compared with a re-optimizing plan. For such cases, an offline adaptive optimization approach can be used less often, for example, on a weekly or biweekly basis, providing correction for accumulated residual errors from multiple fractions rather than a only previous fraction.

Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A system for developing a radiotherapy treatment plan, the system comprising:
a data storage device configured to hold MR image data acquired by an MRI system;
at least one processor configured to:
receive the MR image data from the data storage device;
apply corrections to the MR image data to produce a series of corrected image data;
assemble the series of corrected image data to generate a set of relaxometry maps;
perform a segmentation of a plurality of regions of interest using the set of relaxometry maps;
classify the plurality of regions of interest, using the set of relaxometry maps, to yield a plurality of classified structures;
assign electron density values to the classified structures using an assignment process;
generate, using the electron density values of the classified structures, a set of corrected synthetic electron density images; and
perform a dose calculation using the corrected synthetic electron density images to develop a radiotherapy treatment plan.

2. The system of claim 1, wherein the MR image data comprises 4D MR image data.

3. The system of claim 1, wherein the processor is further configured to apply the corrections using a magnetic field (B0) map, a radio-frequency transmit (B1+) map, or both, to compensate for a magnetic field (B0) inhomogeneity, a RF transmit field (B1+) inhomogeneity, or both.

4. The system of claim 1, wherein the set of relaxometry maps includes a T1 map, a T2 map, a T2* map, or a combination thereof.

5. The system of claim 1, wherein the processor is further configured to classify the plurality of regions of interest according to image intensities in the set of relaxometry maps.

6. The system of claim 1, wherein the processor is further configured to utilize an atlas-based classification technique in the assignment process assigning electron density values to the classified structures.

7. The system of claim 1, wherein the processor is further configured to adapt a radiation treatment plan using the corrected synthetic electron density images according to a treatment optimization process.

8. The system of claim 1, wherein the processor is further configured to correct the set of corrected synthetic electron density images for gradient nonlinearity, or off-resonance effects, field inhomogeneties, or a combination thereof.

9. The system of claim 1, wherein electron density values in the set of corrected synthetic electron density images are used to determine a radiation dose distribution for the dose calculation.

10. A method for producing synthetic images for use in a radiotherapy treatment, the method comprising:
receiving a plurality of magnetic resonance (MR) image data acquired using a magnetic resonance system (MRI) system;
applying corrections to the MR image data to produce a series of corrected image data;
assembling the series of corrected image data to generate a set of relaxometry maps;
performing a segmentation of a plurality of regions of interest using the set of relaxometry maps;
classifying the plurality of regions of interest to yield a plurality of classified structures;
assigning electron density values to the classified structures using an assignment process; and
generating, using the electron density values of the classified structures, a set of corrected synthetic electron density images.

11. The method of claim 10, the method further comprising acquiring, using the MRI system, 3D fast low angle shot (FLASH) images at a plurality of flip angles, 3D balanced steady-state free precession (bSSFP) images at a plurality of flip angles, 3D gradient echo (GRE) images at a plurality of echo times, 3D actual flip angle (AFI) images at a plurality of repetition times, or a combination thereof.

12. The method of claim 10, the method further comprising generating a magnetic field (B0) map, a radio-frequency transmit (B1+) map, or both, to compensate for a magnetic field (B0) inhomogeneity, a RF transmit field (B1+) inhomogeneity, or both.

13. The method of claim 10, wherein the set of relaxometry maps includes a T1 map, a T2 map, a T2* map, or a combination thereof.

14. The method of claim 10, the method further comprising applying a thresholding technique in performing the segmentation.

15. The method of claim 10, the method further comprising classifying the plurality of regions of interest according to image intensities in the set of relaxometry maps to yield the plurality of classified structures.

16. The method of claim 15, the method further comprising utilizing an atlas-based classification technique in the assignment process.

17. The method of claim 10, the method further comprising converting the set of corrected synthetic electron density images to a set of corrected synthetic CT images using an inverted conversion process.

18. The method of claim 10, wherein the set of corrected synthetic electron density images are corrected for at least one of the magnetic field (B0) inhomogeneity, the RF transmit field (B1+) inhomogeneity, and the gradient nonlinearity geometric distortion.

19. The method of claim 10, the method further comprising performing a dose calculation using the corrected synthetic electron density images to develop or adapt a radiotherapy treatment plan.

20. The method of claim 19, wherein electron density values in the set of corrected synthetic electron density images are used to determine a radiation dose distribution for the dose calculation.

* * * * *